(12) United States Patent
Arora et al.

(10) Patent No.: US 12,127,925 B2
(45) Date of Patent: Oct. 29, 2024

(54) WEBS FOR ABSORBENT ARTICLES AND METHODS OF MAKING THE SAME

(71) Applicant: The Procter & Gamble Company, Cincinnati, OH (US)

(72) Inventors: Kelyn A. Arora, Cincinnati, OH (US); John L Hammons, Hamilton, OH (US); Nathan R. Whitely, Liberty Township, OH (US); Misael O. Aviles, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1302 days.

(21) Appl. No.: 16/372,702

(22) Filed: Apr. 2, 2019

(65) Prior Publication Data

US 2019/0314218 A1 Oct. 17, 2019

Related U.S. Application Data

(60) Provisional application No. 62/658,627, filed on Apr. 17, 2018.

(51) Int. Cl.
*A61F 13/513* (2006.01)
*A61F 13/15* (2006.01)
(Continued)

(52) U.S. Cl.
CPC .. *A61F 13/51305* (2013.01); *A61F 13/15764* (2013.01); *A61F 13/15804* (2013.01);
(Continued)

(58) Field of Classification Search
CPC .......... A61F 13/15804; A61F 13/51113; A61F 13/51121; A61F 13/512; A61F 13/514;
(Continued)

(56) References Cited

U.S. PATENT DOCUMENTS

| 3,137,893 A | 6/1964 | Gelpke |
| 3,559,648 A | 2/1971 | Mason, Jr. |

(Continued)

FOREIGN PATENT DOCUMENTS

| CA | 2182304 | 1/1997 |
| CA | 2183776 | 3/1997 |

(Continued)

OTHER PUBLICATIONS

International Search Report and Written Opinion; Application Ser. No.PCT/US2019/027576; dated Apr. 17, 2018, 15 pages.

*Primary Examiner* — Benjamin J Klein
*Assistant Examiner* — Gabriella E Burnette
(74) *Attorney, Agent, or Firm* — Angela K. Haughey; Amanda Herman Berghauer; Christian M. Best

(57) ABSTRACT

The present disclosure is directed, in part, to webs or topsheets for absorbent articles and methods of making the same. The webs and topsheets include bicomponent fibers having a first component and a second component, wherein the first component has a different hydrophilicity than the second component. The webs and topsheets include a continuous land area and discrete zones of modified surface energy. One of the first and second components forms an outer surface of the fibers in the continuous land area and the other of the components at least partially forms an outer surface of the fibers in the discrete zones of modified surface energy such that the discrete zones of modified surface energy have a different hydrophilicity than the continuous land area.

17 Claims, 39 Drawing Sheets

(51) Int. Cl.
    *A61F 13/42*           (2006.01)
    *A61F 13/511*         (2006.01)
    *A61F 13/512*         (2006.01)
    *A61F 13/514*         (2006.01)
    *A61F 13/53*           (2006.01)
    *A61F 13/84*           (2006.01)
    *D04H 1/541*          (2012.01)

(52) U.S. Cl.
    CPC ... *A61F 13/51113* (2013.01); *A61F 13/51121* (2013.01); *A61F 13/512* (2013.01); *A61F 13/514* (2013.01); *A61F 13/53* (2013.01); *D04H 1/5412* (2020.05); *D04H 1/5416* (2020.05); *A61F 2013/15463* (2013.01); *A61F 2013/15715* (2013.01); *A61F 2013/15886* (2013.01); *A61F 2013/422* (2013.01); *A61F 2013/8497* (2013.01); *D04H 1/5414* (2020.05)

(58) Field of Classification Search
    CPC ............ A61F 13/53; A61F 2013/15463; A61F 2013/15715; A61F 2013/15886; A61F 2013/422; A61F 2013/8497; A61F 2013/51338; A61F 2013/51366; A61F 13/513; A61F 13/51104; A61F 13/51305; A61F 13/15764; D04H 1/5412; D04H 1/5416; D04H 1/5414; D04H 1/4291; D04H 1/5405
    See application file for complete search history.

(56) References Cited

U.S. PATENT DOCUMENTS

| | | |
|---|---|---|
| 3,673,026 A | 6/1972 | Brown |
| 3,814,101 A | 6/1974 | Kozak |
| 3,849,845 A | 11/1974 | Obenaus |
| 3,860,003 A | 1/1975 | Buell |
| 3,886,941 A | 6/1975 | Duane et al. |
| 3,890,974 A | 6/1975 | Kozak |
| 3,911,173 A | 10/1975 | Sprague, Jr. |
| 4,137,180 A | 1/1979 | Naik et al. |
| 4,199,464 A | 4/1980 | Cambre |
| 4,306,559 A | 12/1981 | Nishizawa et al. |
| 4,323,069 A | 4/1982 | Ahr et al. |
| 4,324,246 A | 4/1982 | Mullane et al. |
| 4,327,730 A | 5/1982 | Sorensen |
| 4,573,986 A | 3/1986 | Minetola et al. |
| 4,578,414 A | 3/1986 | Sawyer et al. |
| 4,588,630 A | 5/1986 | Shimalla |
| 4,610,678 A | 9/1986 | Goldman et al. |
| 4,629,643 A | 12/1986 | Curro et al. |
| 4,637,819 A | 1/1987 | Ouellette et al. |
| 4,673,402 A | 6/1987 | Weisman et al. |
| 4,676,784 A | 6/1987 | Erdman et al. |
| 4,704,112 A | 11/1987 | Suzuki et al. |
| 4,741,941 A | 5/1988 | Englebert et al. |
| 4,780,352 A | 10/1988 | Palumbo et al. |
| 4,785,996 A | 11/1988 | Ziecker et al. |
| 4,798,604 A | 1/1989 | Carter |
| 4,818,587 A | 4/1989 | Ejima et al. |
| 4,834,735 A | 5/1989 | Alemany et al. |
| 4,840,829 A | 6/1989 | Suzuki et al. |
| 4,842,666 A | 6/1989 | Werenicz |
| 4,888,231 A | 12/1989 | Angstadt |
| 5,108,820 A | 4/1992 | Kaneko et al. |
| 5,122,407 A | 6/1992 | Yeo et al. |
| 5,147,345 A | 9/1992 | Young et al. |
| 5,151,092 A | 9/1992 | Buell et al. |
| 5,234,423 A | 8/1993 | Alemany et al. |
| 5,296,622 A | 3/1994 | Uphues et al. |
| H1377 H | 11/1994 | Perry |
| 5,369,858 A | 12/1994 | Gilmore et al. |
| 5,382,773 A | 1/1995 | Kurihara et al. |
| 5,418,045 A | 5/1995 | Pike et al. |
| 5,433,715 A | 7/1995 | Tanzer et al. |
| 5,437,653 A | 8/1995 | Gilman et al. |
| D362,120 S | 9/1995 | Suskind et al. |
| 5,456,982 A | 10/1995 | Hansen et al. |
| 5,485,662 A | 1/1996 | Hodges, Jr. et al. |
| 5,518,801 A | 5/1996 | Chappell et al. |
| 5,520,673 A | 5/1996 | Yarbrough et al. |
| 5,536,555 A | 7/1996 | Zelazoski et al. |
| 5,571,096 A | 11/1996 | Dobrin et al. |
| 5,597,645 A | 1/1997 | Pike et al. |
| 5,599,335 A | 2/1997 | Goldman et al. |
| 5,605,749 A | 2/1997 | Pike et al. |
| 5,607,760 A | 3/1997 | Roe |
| 5,609,587 A | 3/1997 | Roe |
| 5,628,097 A | 5/1997 | Benson et al. |
| 5,628,737 A | 5/1997 | Dobrin et al. |
| 5,635,191 A | 6/1997 | Roe et al. |
| 5,643,588 A | 7/1997 | Roe et al. |
| 5,643,653 A | 7/1997 | Griesbach et al. |
| 5,660,788 A | 8/1997 | Gray et al. |
| 5,665,083 A | 9/1997 | Igaue et al. |
| 5,667,562 A | 9/1997 | Midkiff |
| 5,667,619 A | 9/1997 | Alikhan |
| 5,704,101 A | 1/1998 | Majors et al. |
| 5,709,735 A | 1/1998 | Midkiff et al. |
| 5,718,698 A | 2/1998 | Dobrin et al. |
| 5,735,984 A | 4/1998 | Hoff et al. |
| H1732 H | 6/1998 | Johnson |
| 5,759,990 A | 6/1998 | Wahl et al. |
| 5,770,144 A | 6/1998 | James et al. |
| 5,780,155 A | 7/1998 | Ishizawa et al. |
| 5,797,894 A | 8/1998 | Cadieux et al. |
| 5,804,021 A | 9/1998 | Abuto et al. |
| 5,824,352 A | 10/1998 | Yang et al. |
| 5,846,230 A | 12/1998 | Osborn, III et al. |
| 5,873,968 A | 2/1999 | Pike et al. |
| 5,874,160 A | 2/1999 | Keck |
| 5,885,267 A | 3/1999 | Mishima et al. |
| 5,895,380 A | 4/1999 | Turi et al. |
| 5,897,541 A | 4/1999 | Uitenbroek et al. |
| 5,897,543 A | 4/1999 | Francis |
| 5,914,084 A | 6/1999 | Benson |
| 5,916,661 A | 6/1999 | Benson et al. |
| 5,919,177 A | 7/1999 | Georger et al. |
| 5,941,864 A | 8/1999 | Roe |
| 5,965,468 A | 10/1999 | Marmon et al. |
| 5,968,025 A | 10/1999 | Roe et al. |
| 5,969,026 A | 10/1999 | Mor et al. |
| 5,998,696 A | 12/1999 | Schone |
| 6,015,936 A | 1/2000 | Takai et al. |
| 6,030,372 A | 2/2000 | Buell et al. |
| 6,093,871 A | 7/2000 | Takai et al. |
| 6,114,595 A | 9/2000 | Moore et al. |
| 6,117,524 A | 9/2000 | Hisanaka et al. |
| 6,159,881 A | 12/2000 | Datta et al. |
| 6,168,849 B1 | 1/2001 | Braverman et al. |
| D439,057 S | 3/2001 | Bissah et al. |
| 6,203,905 B1 | 3/2001 | Pike |
| 6,206,865 B1 | 3/2001 | Chen et al. |
| 6,228,462 B1 | 5/2001 | Lee et al. |
| 6,270,623 B1 | 8/2001 | Goda et al. |
| 6,271,192 B1 | 8/2001 | Verstrat et al. |
| 6,274,237 B1 | 8/2001 | Nakajima et al. |
| 6,303,208 B1 | 10/2001 | Pelkie |
| 6,326,430 B1 | 12/2001 | Berte |
| 6,348,541 B1 | 2/2002 | Kanda et al. |
| 6,361,781 B2 | 3/2002 | Lorant |
| 6,376,456 B1 | 4/2002 | Murphy et al. |
| 6,410,823 B1 | 6/2002 | Daley et al. |
| 6,413,920 B1 | 7/2002 | Bettiol et al. |
| 6,452,064 B1 | 9/2002 | Thoren et al. |
| 6,454,747 B1 | 9/2002 | Shimada et al. |
| 6,454,989 B1 | 9/2002 | Neely et al. |
| 6,468,626 B1 | 10/2002 | Takai et al. |
| 6,475,600 B1 | 11/2002 | Morman et al. |
| 6,479,130 B1 | 11/2002 | Takai et al. |
| 6,494,920 B1 | 12/2002 | Weuthen et al. |
| 6,498,284 B1 | 12/2002 | Roe |
| 6,506,473 B1 | 1/2003 | Hisanaka et al. |

(56) References Cited

U.S. PATENT DOCUMENTS

| | | |
|---|---|---|
| 6,528,439 B1 | 3/2003 | Stokes et al. |
| 6,534,149 B1 | 3/2003 | Daley et al. |
| 6,610,391 B2 | 8/2003 | Molee |
| 6,620,777 B2 | 9/2003 | Heibel et al. |
| 6,632,504 B1 | 10/2003 | Gillespie et al. |
| 6,649,547 B1 | 11/2003 | Arnold et al. |
| 6,676,646 B2 | 1/2004 | Bast et al. |
| 6,716,441 B1 | 4/2004 | Osborne et al. |
| 6,846,561 B1 | 1/2005 | Gownder et al. |
| 6,849,065 B2 | 2/2005 | Schmidt et al. |
| 6,849,319 B2 | 2/2005 | Cree et al. |
| 6,924,261 B2 | 8/2005 | Grandmaire et al. |
| 6,992,058 B2 | 1/2006 | Grandmaire et al. |
| 6,996,851 B2 | 2/2006 | Nordness et al. |
| 7,005,558 B1 | 2/2006 | Johansson et al. |
| 7,033,340 B1 | 4/2006 | Muscat et al. |
| 7,063,895 B2 | 6/2006 | Rodrigues et al. |
| 7,118,639 B2 | 10/2006 | Delucia et al. |
| 7,371,919 B1 | 5/2008 | Busam et al. |
| 7,378,033 B2 | 5/2008 | Harrison et al. |
| 7,381,417 B2 | 6/2008 | Gamez-Garcia |
| 7,803,244 B2 | 9/2010 | Siqueira et al. |
| 7,901,393 B2 | 3/2011 | Matsuda |
| 7,967,801 B2 | 6/2011 | Hammons et al. |
| 7,981,850 B2 | 7/2011 | Doi et al. |
| 8,022,267 B2 | 9/2011 | Hellstroem et al. |
| 8,186,296 B2 | 5/2012 | Brown et al. |
| 8,188,022 B2 | 5/2012 | Sengupta et al. |
| 8,211,414 B2 | 7/2012 | Chen et al. |
| 8,226,625 B2 | 7/2012 | Turner et al. |
| 8,226,626 B2 | 7/2012 | Turner et al. |
| 8,227,660 B2 | 7/2012 | Hara et al. |
| 8,231,595 B2 | 7/2012 | Turner et al. |
| 8,388,594 B2 | 3/2013 | Turner et al. |
| 8,524,649 B2 | 9/2013 | Leyrer et al. |
| 9,018,154 B2 | 4/2015 | Blondel |
| 9,034,230 B2 | 5/2015 | Qureshi et al. |
| 9,237,973 B2 | 1/2016 | Abuto et al. |
| 9,441,188 B2 | 9/2016 | Schramm, Jr. et al. |
| 9,550,309 B2 | 1/2017 | Gibson et al. |
| D778,436 S | 2/2017 | Coslett et al. |
| 9,861,533 B2 | 1/2018 | Hardie et al. |
| 2001/0005540 A1 | 6/2001 | Hisanaka et al. |
| 2001/0008965 A1 | 7/2001 | Kinn et al. |
| 2001/0053901 A1 | 12/2001 | Mizutani et al. |
| 2002/0013563 A1 | 1/2002 | Desai et al. |
| 2002/0022817 A1 | 2/2002 | Ishikawa |
| 2002/0028624 A1 | 3/2002 | Mizutani et al. |
| 2002/0034912 A1 | 3/2002 | Curro et al. |
| 2002/0062113 A1 | 5/2002 | Thomas et al. |
| 2002/0062115 A1 | 5/2002 | Wada et al. |
| 2002/0081927 A1 | 6/2002 | Maldonado et al. |
| 2002/0089079 A1 | 7/2002 | Shelley et al. |
| 2002/0098762 A1 | 7/2002 | Shelley et al. |
| 2002/0098764 A1 | 7/2002 | Mleziva et al. |
| 2002/0132749 A1 | 9/2002 | Smith et al. |
| 2002/0172371 A1 | 11/2002 | Baker et al. |
| 2002/0182371 A1 | 12/2002 | Soon et al. |
| 2002/0182396 A1 | 12/2002 | Delucia et al. |
| 2003/0003269 A1 | 1/2003 | Lee et al. |
| 2003/0004481 A1 | 1/2003 | Matsuoka et al. |
| 2003/0011099 A1 | 1/2003 | Maldonado et al. |
| 2003/0021951 A1 | 1/2003 | Desai et al. |
| 2003/0077430 A1 | 4/2003 | Grimm et al. |
| 2003/0082377 A1 | 5/2003 | Hartzog et al. |
| 2003/0082979 A1 | 5/2003 | Bean et al. |
| 2003/0104748 A1 | 6/2003 | Brown et al. |
| 2003/0109839 A1 | 6/2003 | Costea et al. |
| 2003/0125687 A1 | 7/2003 | Gubernick et al. |
| 2003/0145517 A1 | 8/2003 | Miller |
| 2003/0149412 A1 | 8/2003 | Damaghi et al. |
| 2003/0217945 A1 | 11/2003 | Kiene et al. |
| 2004/0038851 A1 | 2/2004 | Aubay et al. |
| 2004/0043189 A1 | 3/2004 | Huang |
| 2004/0065208 A1 | 4/2004 | Hart et al. |
| 2004/0067709 A1 | 4/2004 | Kishine et al. |
| 2004/0071716 A1 | 4/2004 | Jansen et al. |
| 2004/0092902 A1 | 5/2004 | Schuehle et al. |
| 2004/0116027 A1 | 6/2004 | Termonia et al. |
| 2004/0116321 A1 | 6/2004 | Salesses et al. |
| 2004/0116322 A1 | 6/2004 | Yianakopoulos et al. |
| 2004/0118811 A1 | 6/2004 | Stone et al. |
| 2004/0122396 A1 | 6/2004 | Maldonado et al. |
| 2004/0122404 A1 | 6/2004 | Meyer et al. |
| 2004/0127128 A1 | 7/2004 | Thomas |
| 2004/0127875 A1 | 7/2004 | Hammons et al. |
| 2004/0161586 A1 | 8/2004 | Cree et al. |
| 2004/0162536 A1 | 8/2004 | Becker et al. |
| 2004/0181199 A1 | 9/2004 | Moberg-Alehammar et al. |
| 2004/0204337 A1 | 10/2004 | Corona, III et al. |
| 2004/0209042 A1 | 10/2004 | Peacock et al. |
| 2004/0229769 A1 | 11/2004 | Smith et al. |
| 2005/0003980 A1 | 1/2005 | Baker et al. |
| 2005/0025964 A1 | 2/2005 | Fairbanks et al. |
| 2005/0026527 A1 | 2/2005 | Schmidt et al. |
| 2005/0027270 A1 | 2/2005 | Cree et al. |
| 2005/0096614 A1 | 5/2005 | Perez et al. |
| 2005/0148971 A1 | 7/2005 | Kuroda et al. |
| 2005/0175385 A1 | 8/2005 | Cho et al. |
| 2005/0202208 A1 | 9/2005 | Kelly |
| 2005/0233140 A1 | 10/2005 | Oh et al. |
| 2005/0244619 A1 | 11/2005 | Kauschke et al. |
| 2005/0256027 A1 | 11/2005 | Heibel et al. |
| 2005/0256475 A1 | 11/2005 | Komatsu et al. |
| 2005/0288647 A1 | 12/2005 | Ellingson et al. |
| 2006/0019063 A1 | 1/2006 | Kelly |
| 2006/0020251 A1 | 1/2006 | Kelly |
| 2006/0068176 A1 | 3/2006 | Zafiroglu et al. |
| 2006/0069361 A1 | 3/2006 | Olson |
| 2006/0087053 A1 | 4/2006 | O'Donnell et al. |
| 2006/0107505 A1 | 5/2006 | Desai et al. |
| 2006/0135026 A1 | 6/2006 | Arendt et al. |
| 2006/0135923 A1 | 6/2006 | Boggs et al. |
| 2006/0141885 A1 | 6/2006 | Cobbs et al. |
| 2006/0148358 A1 | 7/2006 | Hall et al. |
| 2006/0252669 A1 | 11/2006 | Heibel et al. |
| 2007/0015427 A1 | 1/2007 | Yanagawase et al. |
| 2007/0021022 A1 | 1/2007 | Kishine et al. |
| 2007/0036943 A1 | 2/2007 | Hirose et al. |
| 2007/0048498 A1 | 3/2007 | Cree |
| 2007/0073254 A1 | 3/2007 | Ponomarenko et al. |
| 2007/0088307 A1 | 4/2007 | Arizti et al. |
| 2007/0099817 A1 | 5/2007 | Smith et al. |
| 2007/0135787 A1 | 6/2007 | Raidel et al. |
| 2007/0256286 A1 | 11/2007 | Ngai |
| 2007/0275622 A1 | 11/2007 | Masuda et al. |
| 2007/0275866 A1 | 11/2007 | Dykstra |
| 2007/0293413 A1 | 12/2007 | McFarland et al. |
| 2008/0076692 A1 | 3/2008 | Carvell et al. |
| 2008/0138574 A1 | 6/2008 | Maschino et al. |
| 2008/0143009 A1 | 6/2008 | Kurian et al. |
| 2008/0294135 A1 | 11/2008 | Hara et al. |
| 2008/0294138 A1 | 11/2008 | Andersson et al. |
| 2008/0295256 A1 | 12/2008 | Broze et al. |
| 2008/0300562 A1 | 12/2008 | Ahoniemi et al. |
| 2008/0312343 A1 | 12/2008 | Braun et al. |
| 2008/0312622 A1 | 12/2008 | Beruda et al. |
| 2008/0317984 A1 | 12/2008 | Yamashita et al. |
| 2009/0030390 A1 | 1/2009 | Hammons et al. |
| 2009/0030391 A1 | 1/2009 | Hammons et al. |
| 2009/0082746 A1 | 3/2009 | Thomas et al. |
| 2009/0104831 A1 | 4/2009 | Bornemann et al. |
| 2009/0124155 A1 | 5/2009 | Tiemeier et al. |
| 2009/0131896 A1 | 5/2009 | Ebitsuka et al. |
| 2009/0191779 A1 | 7/2009 | Cree |
| 2009/0233046 A1 | 9/2009 | Iulianetti |
| 2009/0247978 A1 | 10/2009 | Boissier |
| 2009/0259208 A1 | 10/2009 | Hellstrom et al. |
| 2009/0299316 A1 | 12/2009 | Seyler |
| 2009/0318050 A1 | 12/2009 | Okaya |
| 2010/0004615 A1 | 1/2010 | Boissier |
| 2010/0019415 A1 | 1/2010 | Stone et al. |
| 2010/0035014 A1 | 2/2010 | Hammons et al. |
| 2010/0036338 A1 | 2/2010 | Hammons et al. |

(56) References Cited

U.S. PATENT DOCUMENTS

| | | |
|---|---|---|
| 2010/0036346 A1 | 2/2010 | Hammons et al. |
| 2010/0100067 A1 | 4/2010 | Pugliese, III |
| 2010/0105273 A1 | 4/2010 | Motomura et al. |
| 2010/0130952 A1 | 5/2010 | Murai |
| 2010/0159770 A1 | 6/2010 | Walser et al. |
| 2010/0164733 A1 | 7/2010 | Ales et al. |
| 2010/0190679 A1 | 7/2010 | Vanpachtenbeke et al. |
| 2010/0196653 A1 | 8/2010 | Curro et al. |
| 2010/0227130 A1 | 9/2010 | Takahashi |
| 2010/0233438 A1 | 9/2010 | Stone et al. |
| 2010/0252138 A1 | 10/2010 | Tseng |
| 2010/0261399 A1 | 10/2010 | Katsuya et al. |
| 2010/0280471 A1 | 11/2010 | Shah |
| 2010/0330326 A1 | 12/2010 | Turner et al. |
| 2011/0024940 A1 | 2/2011 | Khalid et al. |
| 2011/0046592 A1 | 2/2011 | Nishikawa et al. |
| 2011/0106036 A1 | 5/2011 | Staahl et al. |
| 2011/0184370 A1 | 7/2011 | Seyler et al. |
| 2011/0189915 A1 | 8/2011 | Morimoto et al. |
| 2011/0196330 A1 | 8/2011 | Hammons et al. |
| 2011/0236683 A1 | 9/2011 | Takebe et al. |
| 2011/0245141 A1 | 10/2011 | Gizaw et al. |
| 2011/0269663 A1 | 11/2011 | Clowes et al. |
| 2011/0301312 A1 | 12/2011 | Blondel |
| 2011/0305870 A1 | 12/2011 | Curro et al. |
| 2011/0313385 A1 | 12/2011 | Hammons et al. |
| 2012/0003423 A1 | 1/2012 | Cree et al. |
| 2012/0035566 A1 | 2/2012 | Sagisaka et al. |
| 2012/0077886 A1 | 3/2012 | Scholz et al. |
| 2012/0095426 A1 | 4/2012 | Visscher et al. |
| 2012/0121882 A1 | 5/2012 | Okaya |
| 2012/0171913 A1 | 7/2012 | Fox et al. |
| 2012/0273990 A1 | 11/2012 | O'Donnell et al. |
| 2012/0282436 A1 | 11/2012 | Coe et al. |
| 2012/0295060 A1 | 11/2012 | Mullane |
| 2012/0296304 A1 | 11/2012 | Choo et al. |
| 2013/0012898 A1 | 1/2013 | Bergendahl et al. |
| 2013/0029555 A1 | 1/2013 | Morimoto |
| 2013/0109612 A1 | 5/2013 | Corona, III et al. |
| 2013/0121944 A1 | 5/2013 | Leyrer et al. |
| 2013/0121945 A1 | 5/2013 | Leyrer et al. |
| 2013/0129657 A1 | 5/2013 | Streuli |
| 2013/0139666 A1 | 6/2013 | Raidel et al. |
| 2013/0097101 A1 | 8/2013 | Braun et al. |
| 2013/0253461 A1 | 9/2013 | Xu et al. |
| 2013/0310300 A1 | 11/2013 | Leyrer et al. |
| 2013/0310301 A1 | 11/2013 | Sivik et al. |
| 2014/0000784 A1* | 1/2014 | Rane ............... D04H 13/00 156/62.8 |
| 2014/0031779 A1 | 1/2014 | Hammons et al. |
| 2014/0047649 A1 | 2/2014 | Blondel |
| 2014/0066873 A1 | 3/2014 | Kawakami et al. |
| 2014/0087130 A1 | 3/2014 | Seyler et al. |
| 2014/0121624 A1 | 5/2014 | Kirby et al. |
| 2014/0148774 A1 | 5/2014 | Brown et al. |
| 2014/0151934 A1 | 6/2014 | Thomas et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0296809 A1 | 10/2014 | Hammons et al. |
| 2014/0296815 A1 | 10/2014 | Takken et al. |
| 2014/0303581 A1 | 10/2014 | Karlsson |
| 2014/0315779 A1 | 10/2014 | Zander |
| 2014/0324009 A1 | 10/2014 | Lee et al. |
| 2014/0336605 A1 | 11/2014 | Hardie et al. |
| 2014/0378639 A1 | 12/2014 | Blondel et al. |
| 2015/0191677 A1 | 7/2015 | Blondel |
| 2015/0197708 A1 | 7/2015 | Jin |
| 2015/0209189 A1 | 7/2015 | Mullane |
| 2015/0283001 A1 | 10/2015 | Arizti et al. |
| 2015/0283003 A1 | 10/2015 | Rosati et al. |
| 2015/0329799 A1 | 11/2015 | Schramm, Jr. et al. |
| 2015/0337239 A1 | 11/2015 | Gonzalez De Cossio et al. |
| 2016/0024426 A1 | 1/2016 | Sivik et al. |
| 2016/0024427 A1 | 1/2016 | Sivik et al. |
| 2016/0024428 A1 | 1/2016 | Dykstra et al. |
| 2016/0024429 A1 | 1/2016 | Dykstra et al. |
| 2016/0024430 A1 | 1/2016 | Dykstra et al. |
| 2016/0024431 A1 | 1/2016 | Dykstra et al. |
| 2016/0024432 A1 | 1/2016 | Sivik et al. |
| 2016/0024434 A1 | 1/2016 | Sivik et al. |
| 2016/0032220 A1 | 2/2016 | Sivik et al. |
| 2016/0129626 A1 | 5/2016 | Arora et al. |
| 2016/0136010 A1 | 5/2016 | Roe et al. |
| 2016/0136016 A1 | 5/2016 | Mullane et al. |
| 2016/0167334 A1* | 6/2016 | Arora ............... A61F 13/51478 428/137 |
| 2017/0258651 A1 | 9/2017 | Hammons |
| 2017/0258955 A1 | 9/2017 | Lindner et al. |
| 2017/0319403 A1* | 11/2017 | Bewick-Sonntag .... A61F 13/47 |
| 2018/0256773 A1 | 9/2018 | Lindner et al. |

FOREIGN PATENT DOCUMENTS

| | | |
|---|---|---|
| CA | 2733472 | 9/2009 |
| CA | 2482306 C | 10/2011 |
| CN | 2567250 | 8/2003 |
| CN | 1772984 | 5/2006 |
| CN | 2897211 | 5/2007 |
| CN | 202724134 U | 11/2009 |
| CN | 201505226 | 6/2010 |
| CN | 201618014 | 11/2010 |
| CN | 201855363 | 6/2011 |
| CN | 101724132 B | 11/2011 |
| CN | 101940514 B | 12/2013 |
| DE | 2806401 | 8/1979 |
| DE | 4106295 | 9/1992 |
| DE | 19647459 | 5/1998 |
| DE | 19846857 | 3/2000 |
| EP | 165807 | 12/1985 |
| EP | 0 172 025 A2 | 2/1986 |
| EP | 0 172 723 A2 | 2/1986 |
| EP | 0 172 724 A2 | 2/1986 |
| EP | 0 330 212 | 8/1989 |
| EP | 0 343 840 A2 | 11/1989 |
| EP | 359501 | 3/1990 |
| EP | 495212 | 7/1992 |
| EP | 535579 | 4/1993 |
| EP | 545423 | 6/1993 |
| EP | 0589224 | 3/1994 |
| EP | 0 691 427 | 1/1996 |
| EP | 0 696 655 | 2/1996 |
| EP | 749736 | 12/1996 |
| EP | 749737 | 12/1996 |
| EP | 749738 | 12/1996 |
| EP | 749739 | 12/1996 |
| EP | 749740 | 12/1996 |
| EP | 0 761 846 A2 | 3/1997 |
| EP | 0934737 | 8/1999 |
| EP | 983758 | 3/2000 |
| EP | 1022007 | 7/2000 |
| EP | 1040807 | 10/2000 |
| EP | 1086676 | 3/2001 |
| EP | 0710472 | 4/2001 |
| EP | 1066006 | 5/2003 |
| EP | 1 352 948 | 10/2003 |
| EP | 1 140 228 | 3/2004 |
| EP | 1 625 195 B1 | 5/2007 |
| EP | 1 740 682 B1 | 6/2009 |
| EP | 1 756 168 B1 | 7/2009 |
| EP | 2 110 472 | 10/2009 |
| EP | 2 284 250 | 2/2011 |
| EP | 2347872 | 7/2011 |
| EP | 1 781 717 B1 | 11/2012 |
| EP | 1 988 793 | 7/2014 |
| FR | 2862975 B1 | 2/2006 |
| GB | 2 002 400 A | 2/1979 |
| GB | 2103933 | 3/1983 |
| GB | 2225724 | 6/1990 |
| GB | 2296464 | 7/1996 |
| GB | 2310606 | 9/1997 |
| JP | 04327256 | 11/1992 |
| JP | H 042327211 | 11/1992 |
| JP | H 05195406 | 8/1993 |

(56) References Cited

FOREIGN PATENT DOCUMENTS

| | | |
|---|---|---|
| JP | 6038818 | 2/1994 |
| JP | H 07216653 | 8/1995 |
| JP | 2587116 | 3/1997 |
| JP | 09059823 | 3/1997 |
| JP | 09310226 | 12/1997 |
| JP | 10272152 | 10/1998 |
| JP | 11152624 | 6/1999 |
| JP | 2001032139 | 2/2001 |
| JP | 2002180331 | 6/2002 |
| JP | 2003003334 | 1/2003 |
| JP | 2004041870 | 2/2004 |
| JP | 2005200795 | 7/2005 |
| JP | 2008127705 | 6/2008 |
| JP | 2008174880 | 7/2008 |
| JP | 2008179939 | 8/2008 |
| JP | 2009050621 | 3/2009 |
| JP | 2009-172354 | 8/2009 |
| JP | 4357591 | 11/2009 |
| JP | 2010269029 | 12/2010 |
| JP | 2011135979 | 7/2011 |
| JP | 2011239835 | 12/2011 |
| JP | 2012050548 | 3/2012 |
| JP | 2012154010 A | 8/2012 |
| JP | 2012158547 A | 8/2012 |
| JP | 5034078 B2 | 9/2012 |
| JP | 2013011051 | 1/2013 |
| JP | 2014034741 | 2/2014 |
| JP | 5528660 B2 | 6/2014 |
| KR | 2001064584 | 7/2001 |
| KR | 20030089593 | 11/2003 |
| KR | 100648560 | 11/2006 |
| KR | 20150100549 A | 9/2015 |
| WO | WO 91-10415 | 7/1991 |
| WO | WO 93-11726 | 6/1993 |
| WO | WO 93-15701 | 8/1993 |
| WO | WO 95-13773 | 5/1995 |
| WO | WO 95-17867 | 7/1995 |
| WO | WO 1996-007689 | 3/1996 |
| WO | WO 96-10481 | 4/1996 |
| WO | WO 96-11107 | 4/1996 |
| WO | WO 96-19313 | 6/1996 |
| WO | WO 1996-021759 | 7/1996 |
| WO | WO 97-02133 | 1/1997 |
| WO | WO 2007-01320 | 1/1997 |
| WO | WO 97-03818 | 2/1997 |
| WO | WO 1997-09020 | 3/1997 |
| WO | WO 1997-11661 | 4/1997 |
| WO | WO 1998-053896 | 12/1998 |
| WO | WO 1999-020725 | 4/1999 |
| WO | WO-9930660 | 6/1999 |
| WO | WO 9939671 | 8/1999 |
| WO | WO 1999-060975 | 12/1999 |
| WO | WO 2000-001334 | 1/2000 |
| WO | WO 2000-013636 | 3/2000 |
| WO | WO 2000-024351 | 5/2000 |
| WO | WO 2000-028929 | 5/2000 |
| WO | WO 2000-037249 | 6/2000 |
| WO | WO 2000-062826 | 10/2000 |
| WO | 0171080 A1 | 9/2001 |
| WO | WO 2001-072251 | 10/2001 |
| WO | WO 2002-057400 A2 | 7/2002 |
| WO | WO 2002-100632 | 12/2002 |
| WO | WO 2003-002699 | 1/2003 |
| WO | WO 2003-008688 A2 | 1/2003 |
| WO | WO 2003-015681 | 2/2003 |
| WO | WO 03024706 | 3/2003 |
| WO | WO 2003-071019 | 8/2003 |
| WO | WO 2003-102043 | 12/2003 |
| WO | WO 2004-009009 | 1/2004 |
| WO | WO 2004-050812 | 6/2004 |
| WO | WO 2004-058497 | 7/2004 |
| WO | WO 2004-061065 | 7/2004 |
| WO | WO 2004-098474 | 11/2004 |
| WO | WO 2005-087907 | 9/2005 |
| WO | WO 2005-097834 A2 | 10/2005 |
| WO | WO 2005-103215 | 11/2005 |
| WO | WO 2008-005693 A2 | 1/2008 |
| WO | WO 2010-078959 | 7/2010 |
| WO | WO 2010-079100 | 7/2010 |
| WO | WO 2010-141309 | 12/2010 |
| WO | WO 2011-017285 | 2/2011 |
| WO | WO-2011-080643 | 7/2011 |
| WO | WO 2012-14957 | 2/2012 |
| WO | WO 2012-052172 | 4/2012 |
| WO | WO 2012-076432 | 6/2012 |
| WO | WO 2013-068388 | 5/2013 |
| WO | WO 2013-068394 | 5/2013 |
| WO | WO 2013-91150 | 6/2013 |
| WO | WO 2013-114231 | 8/2013 |
| WO | WO 2013-142486 | 9/2013 |
| WO | WO-2013-147222 | 10/2013 |
| WO | WO 2013-189010 | 12/2013 |
| WO | WO 2014-022652 | 2/2014 |
| WO | WO 2014-108106 | 7/2014 |
| WO | WO 2015-130088 | 9/2015 |
| WO | WO 2015-157254 | 10/2015 |
| WO | WO-2017158487 A1 * | 9/2017 ....... A61F 13/15731 |

* cited by examiner

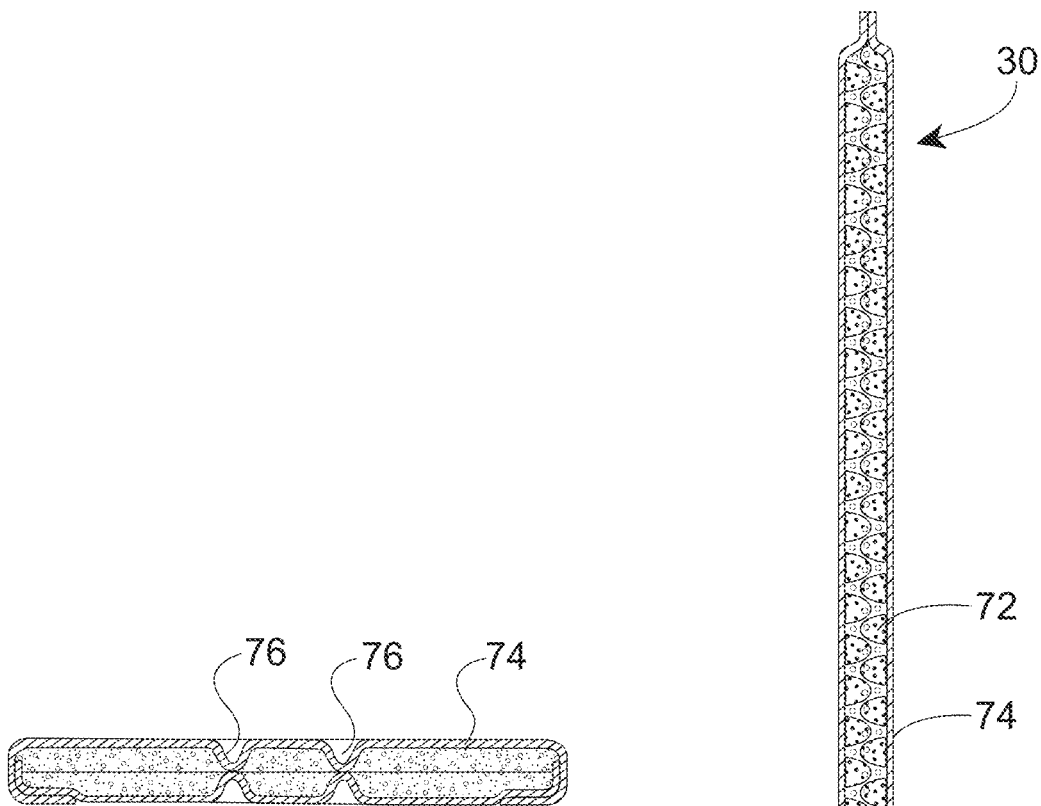
Fig. 10
Fig. 11

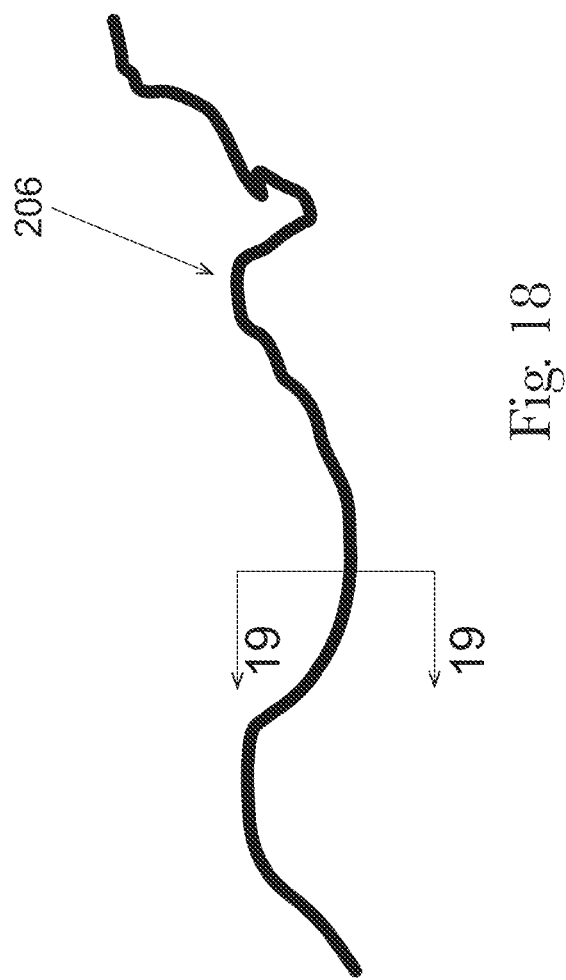

WEBS FOR ABSORBENT ARTICLES AND METHODS OF MAKING THE SAME

CROSS REFERENCE TO RELATED APPLICATION

This application claims the benefit, under 35 U.S.C. § 119(e), to U.S. Provisional Patent Application No. 62/658,627, filed on Apr. 17, 2018, which is herein incorporated by reference in its entirety.

FIELD

The present disclosure is generally directed to webs or topsheets for absorbent articles and methods of making the same.

BACKGROUND

Absorbent articles are used to contain and absorb bodily exudates (i.e., urine, bowel movements, and menses). Absorbent articles may take on the form of diapers, pants, adult incontinence garments, sanitary napkins, and/or tampons, for example. These absorbent articles typically comprise a liquid permeable topsheet, a liquid impermeable backsheet, and an absorbent core positioned at least partially intermediate the topsheet and the backsheet. The absorbent articles may also comprise an acquisition layer or a secondary topsheet positioned at least partially intermediate the topsheet and the absorbent core. Some current apertured topsheets (ATS) for absorbent articles employ a fully hydrophobic nonwoven topsheet with large apertures (e.g., 2-5 $mm^2$) and a high open area (e.g., 30%) to deliver a clean and dry topsheet. The large apertures allow for rapid bodily exudate acquisition, while the hydrophobic fibers enable low rewet and prevent, or at least inhibit, bodily exudate retention in the topsheet. Typically, smaller apertures (e.g., less than 1.5 $mm^2$ or less than 1 $mm^2$) cannot be provided in fully hydrophobic topsheets because the bodily exudates will not penetrate through the smaller apertures owing to surface tensions and viscosities of the bodily exudates. Smaller apertures e.g., less than 1.5 $mm^2$ or less than 1 $mm^2$ and lower open areas (e.g., less than 20%, or less than 15%), however, may be desired in topsheets for softness and aesthetics (i.e., patterning). In order to maintain sufficient bodily exudate handling, some absorbent article manufacturers have utilized a dual layer topsheet approach (hydrophobic layer over a hydrophilic layer) with these smaller apertures and reduced open areas. In order to reduce costs and complexities, it is desired to provide a single layer web or topsheet that can still deliver the same bodily exudate handling and aesthetics as two layer laminates and with the smaller apertures and the smaller open areas. Additionally, it is desired to selectively "activate" hydrophilic character only in selected regions of webs or topsheets in order to better control bodily exudate movement. Alternatively, it may be desired to selectively activate hydrophobic character only in selected regions of webs or topsheets, with the rest of the webs or topsheets remaining hydrophilic. Therefore, webs and topsheets should be improved.

SUMMARY

The present disclosure provides webs or topsheets for absorbent articles that overcome the drawbacks of large apertured, hydrophobic topsheets (ATS) and smaller apertured duel layer topsheets (hydrophobic layer over hydrophilic layer) by providing a single layer web or topsheet that comprises discrete zones of modified surface energy. The webs or topsheet may also comprise continuous land areas or a plurality of land areas that may or may not be continuous. The webs or topsheets may comprise fibers. The fibers may comprise bicomponent fibers each comprising a first component and a second component. At least some of the first components may comprise a hydrophobic resin or a hydrophobic melt additive. At least some of the second components may comprise a hydrophilic resin or a hydrophilic melt additive. At least some of the discrete zones of modified surface energy comprising the bicomponent fibers may be surrounded by the continuous land area. In the continuous land area, the second components may not be exposed to maintain the continuous land area hydrophobic, even after any spontaneous blooming of the hydrophilic melt additive in the second components. In at least some of the discrete zones of modified surface energy, the second components may be at least partially exposed (not relating to spontaneous blooming of the hydrophilic melt additive) to render the discrete zones of modified surface energy hydrophilic, or at least partially hydrophilic. The discrete zones of modified surface energy are not created by a hydrophilic melt additive and/or a spontaneously blooming. Instead, these discrete zones of modified surface energy are created/exposed by heat and/or energy after any spontaneous blooming of the hydrophilic melt additive and/or the hydrophobic melt additive occurs and the blooming reaches some equilibrium state. By providing bicomponent fibers with the first and second components having different hydrophilicities, the discrete zones of modified surface energy may have a different hydrophilicity than the continuous land area surrounding them or the plurality of land areas. This can be accomplished in a single layer web compared to a dual layer web (i.e., hydrophobic layer over hydrophilic layer), which can save significant material costs. In the single layer apertured web or topsheet context, the apertures may be smaller than the large apertures in ATS to promote softness and aesthetics (e.g., patterning). Perimeters of the apertures, or portions thereof, may correspond to the discrete zones of modified surface energy, whether pin apertured, overbonded and ring rolled to form apertures, or formed by other aperturing processes. The single layer web or topsheet may have discrete zones of modified surface energy without the use of a topical surface energy modifying treatments or printed surface energy modifying treatments. Stated another way, the single layer web or topsheet may be free of topical or printed surface energy modifying treatments. It is noted, however, that this does not exclude a lotion etc. from being applied to the webs or topsheets.

The present disclosure is directed, in part, to an absorbent article comprising a nonwoven topsheet, a backsheet, and an absorbent core positioned at least partially intermediate the topsheet and the backsheet. The topsheet may be a single layer material, but could be joined with other materials to form a laminate. The nonwoven topsheet may comprise a plurality of bicomponent fibers forming the nonwoven topsheet. At least some of the bicomponent fibers each comprise a first component and a second component. The first component may comprise a hydrophobic resin or a hydrophobic melt additive and the second component may comprise a hydrophilic resin or a hydrophilic melt additive. The nonwoven topsheet may comprise a continuous land area comprising the bicomponent fibers and discrete zones of modified surface energy comprising the bicomponent fibers. At least a majority of the discrete zones of modified surface energy may be surrounded by the continuous land area. In the continuous land area, the second component may not be exposed to maintain the continuous land area hydrophobic. In at least some of the discrete zones of modified surface energy, the second component may be at least partially exposed to render the discrete zones of modified surface energy hydrophilic. The topsheet may be free of topical or printed surface energy modifying treatments.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 10 is a cross-sectional view, taken about line 10-10, of the absorbent core of FIG. 9;

FIG. 11 is a cross-sectional view, taken about line 11-11, of the absorbent core of FIG. 10;

FIG. 18 is a side view of a single bicomponent fiber;

DETAILED DESCRIPTION

Various non-limiting forms of the present disclosure will now be described to provide an overall understanding of the principles of the structure, function, manufacture, and use of the webs for absorbent articles and methods for making the same disclosed herein. One or more examples of these non-limiting forms are illustrated in the accompanying drawings. Those of ordinary skill in the art will understand that the webs for absorbent articles and methods for making the same described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein "hydrophilic" and "hydrophobic" have meanings well established in the art with respect to the contact angle of a referenced liquid on the surface of a material. Thus, a material having a liquid (water) contact angle of greater than about 90 degrees is considered hydrophobic, and a material having a liquid (water) contact angle of less than about 90 degrees is considered hydrophilic.

Initially, a general description of example absorbent articles will be provided and then the webs or topsheet for absorbent articles and methods of making the same will be discussed. The webs may be used in consumer products other than absorbent articles. The webs for absorbent articles may form a topsheet, an acquisition layer, a distribution layer, a secondary topsheet, a core cover, a portion of an elastic belt, other suitable layers, or a web in a consumer products other than absorbent articles.

General Description of an Absorbent Article

Figure 1:
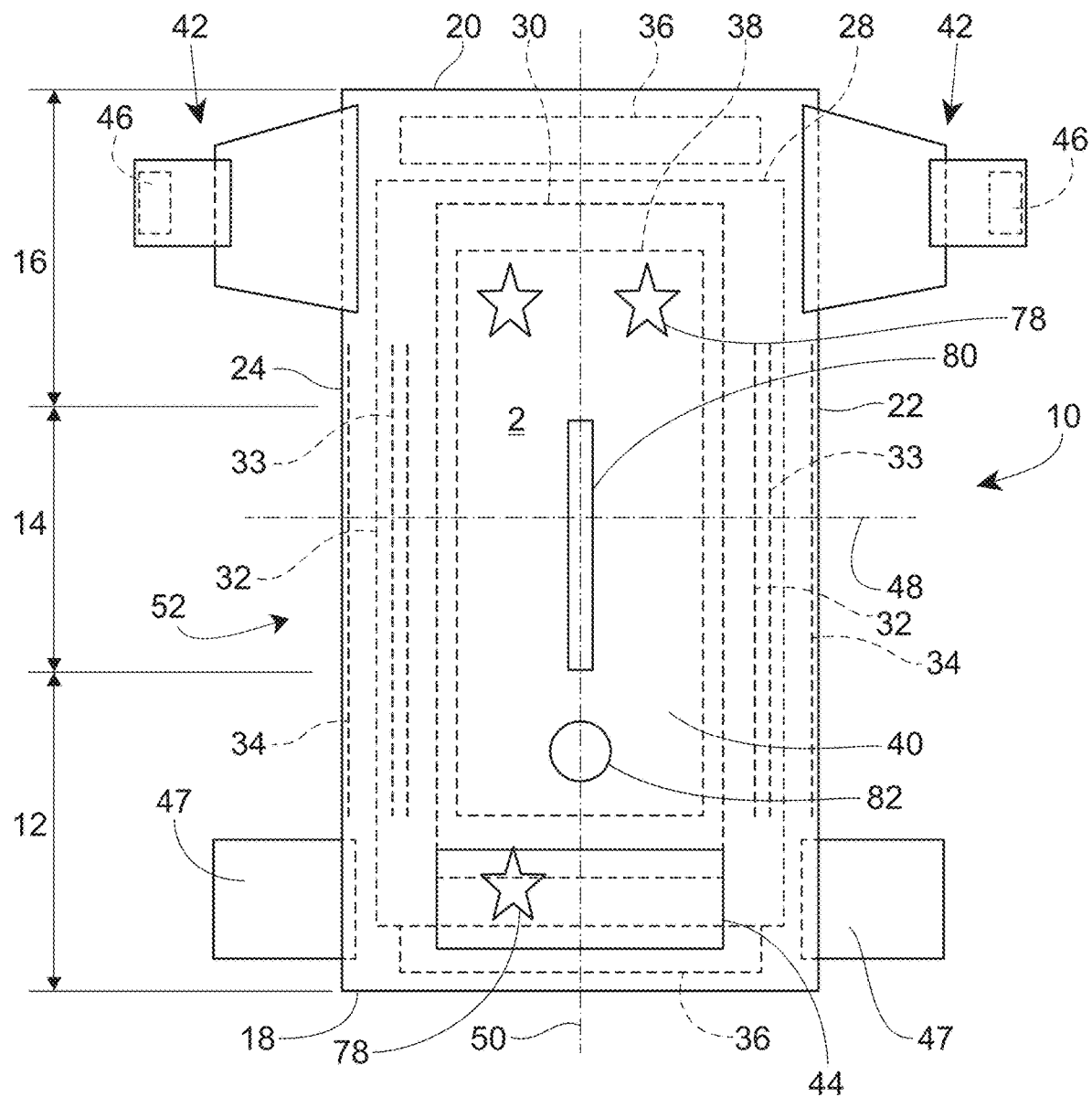
FIG. 1 is a plan view of an example absorbent article in the form of a taped diaper, garment-facing surface facing the viewer, in a flat laid-out state.
Figure 2:
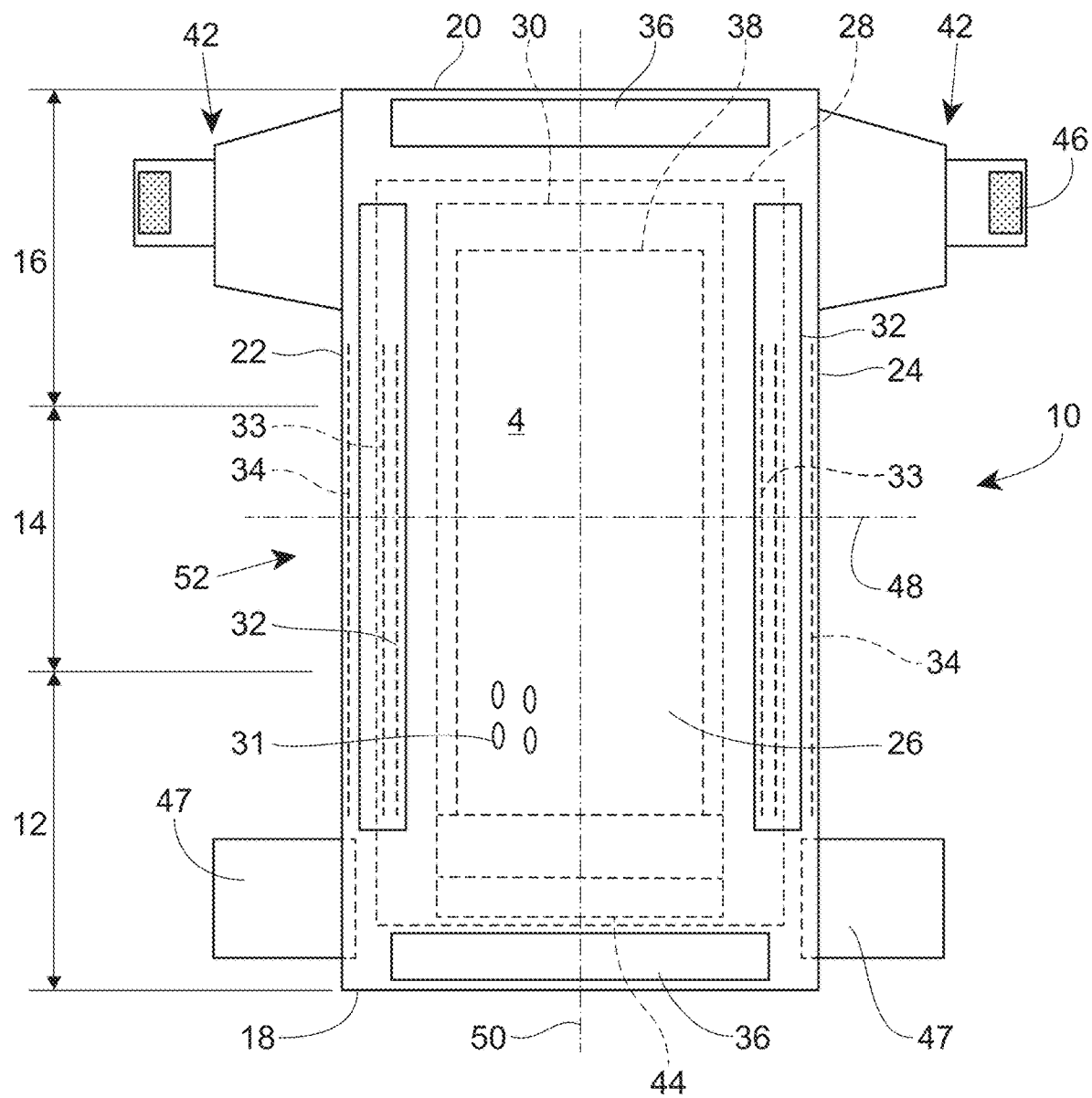
FIG. 2 is a plan view of the example absorbent article of FIG. 1, wearer-facing surface facing the viewer, in a flat laid-out state.
Figure 3:
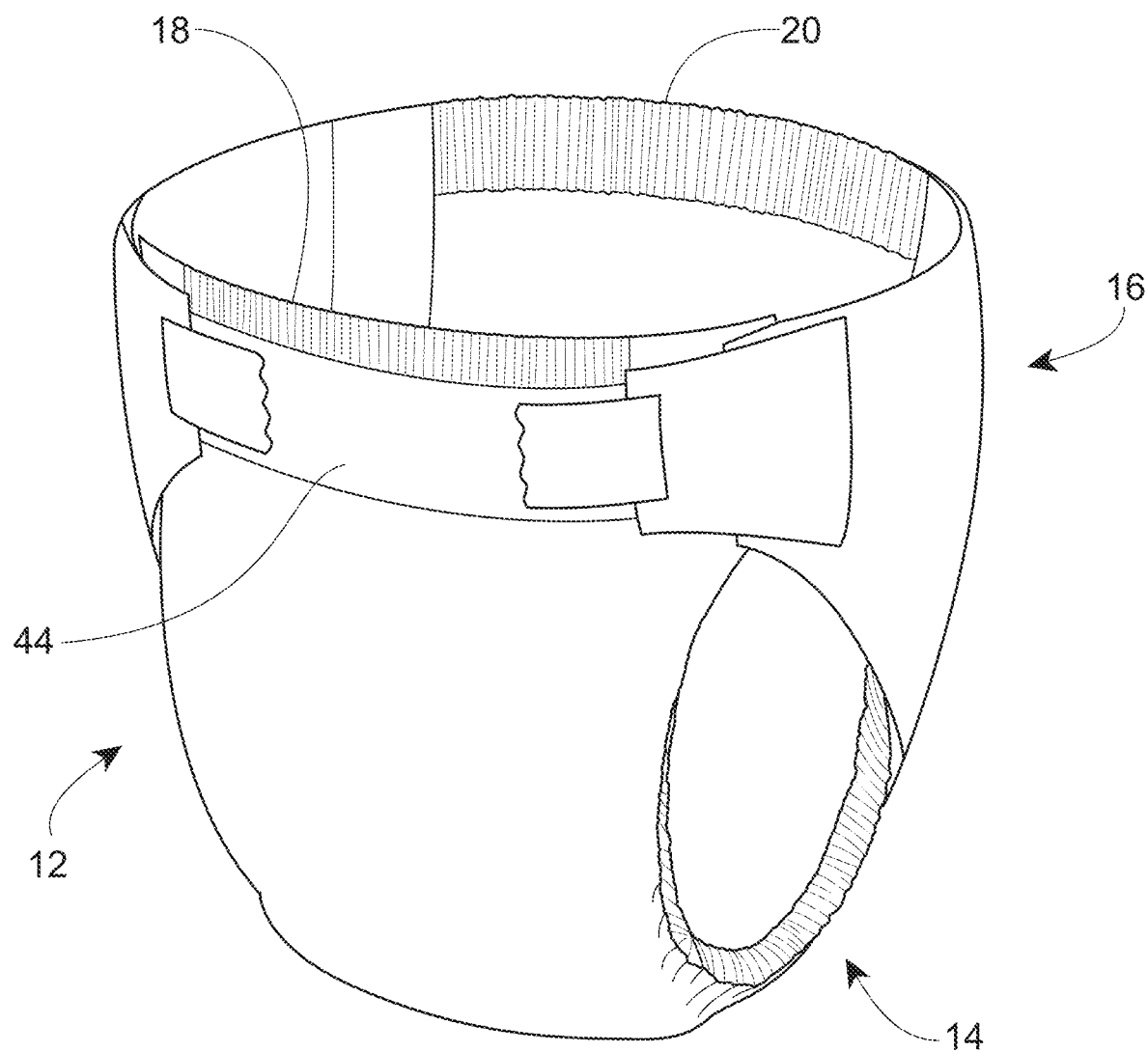
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
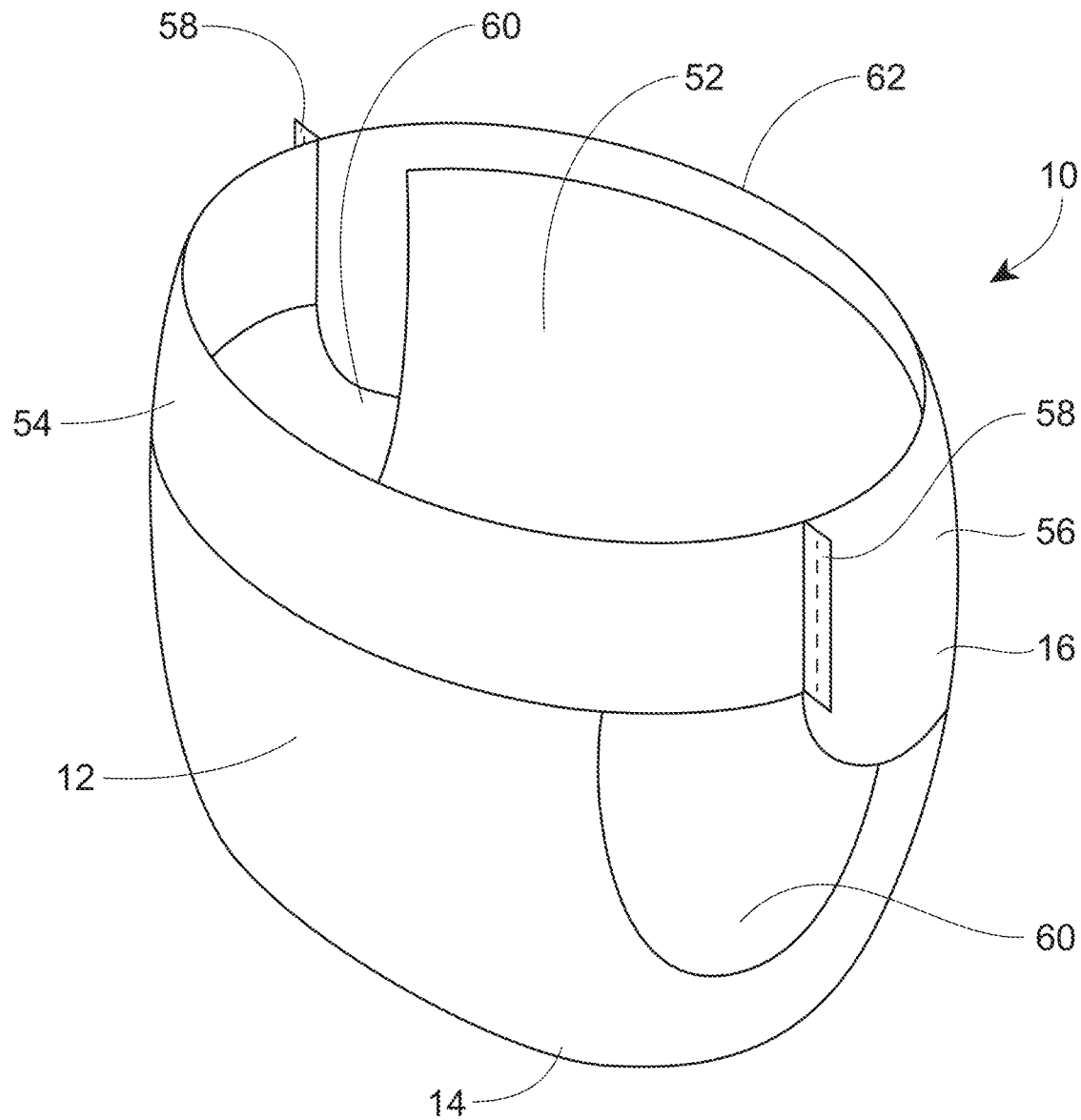
FIG. 4 is a front perspective view of an absorbent article in the form of a pant.
Figure 5:
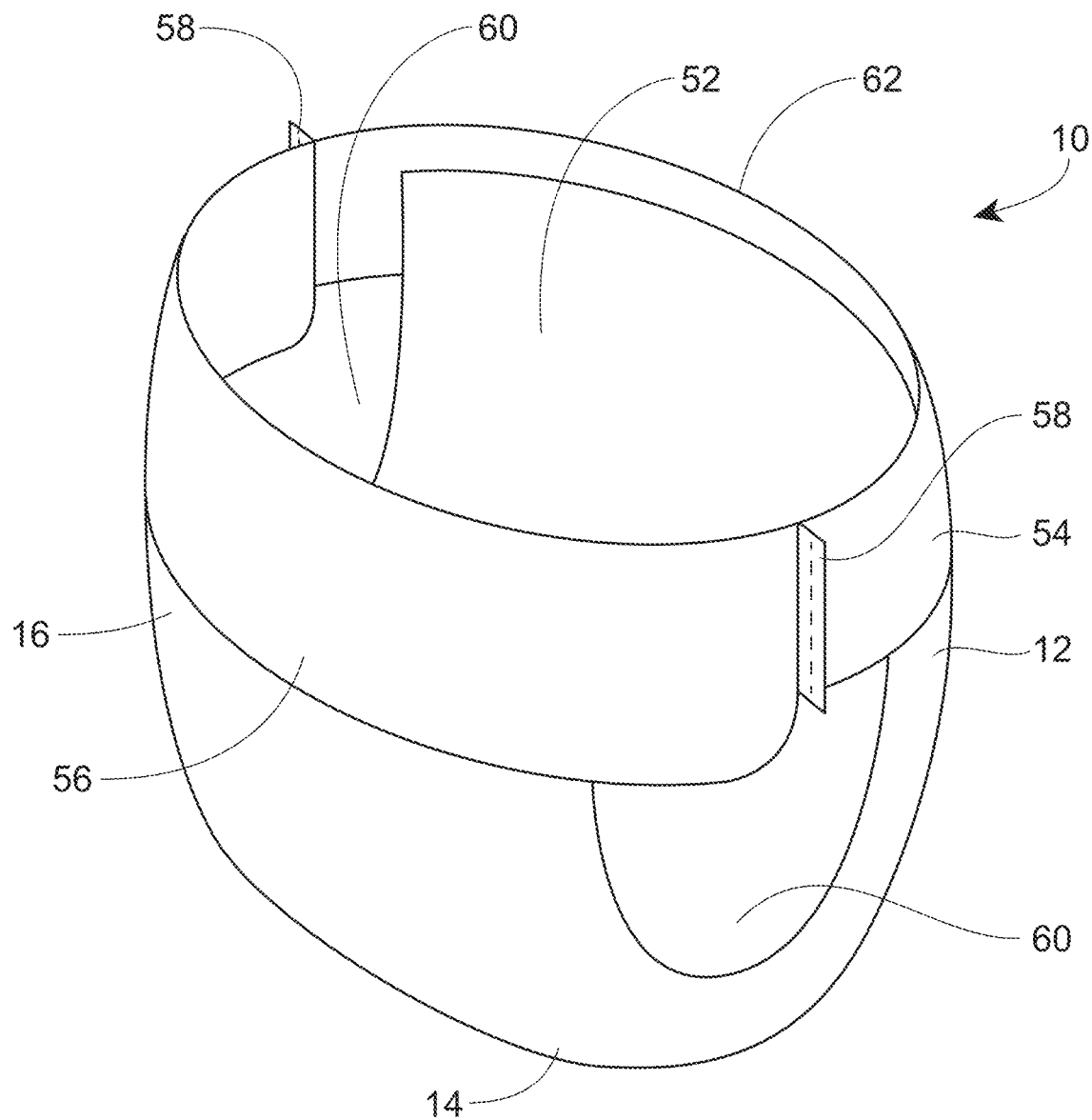
FIG. 5 is a rear perspective view of the absorbent article of FIG. 4.
Figure 6:
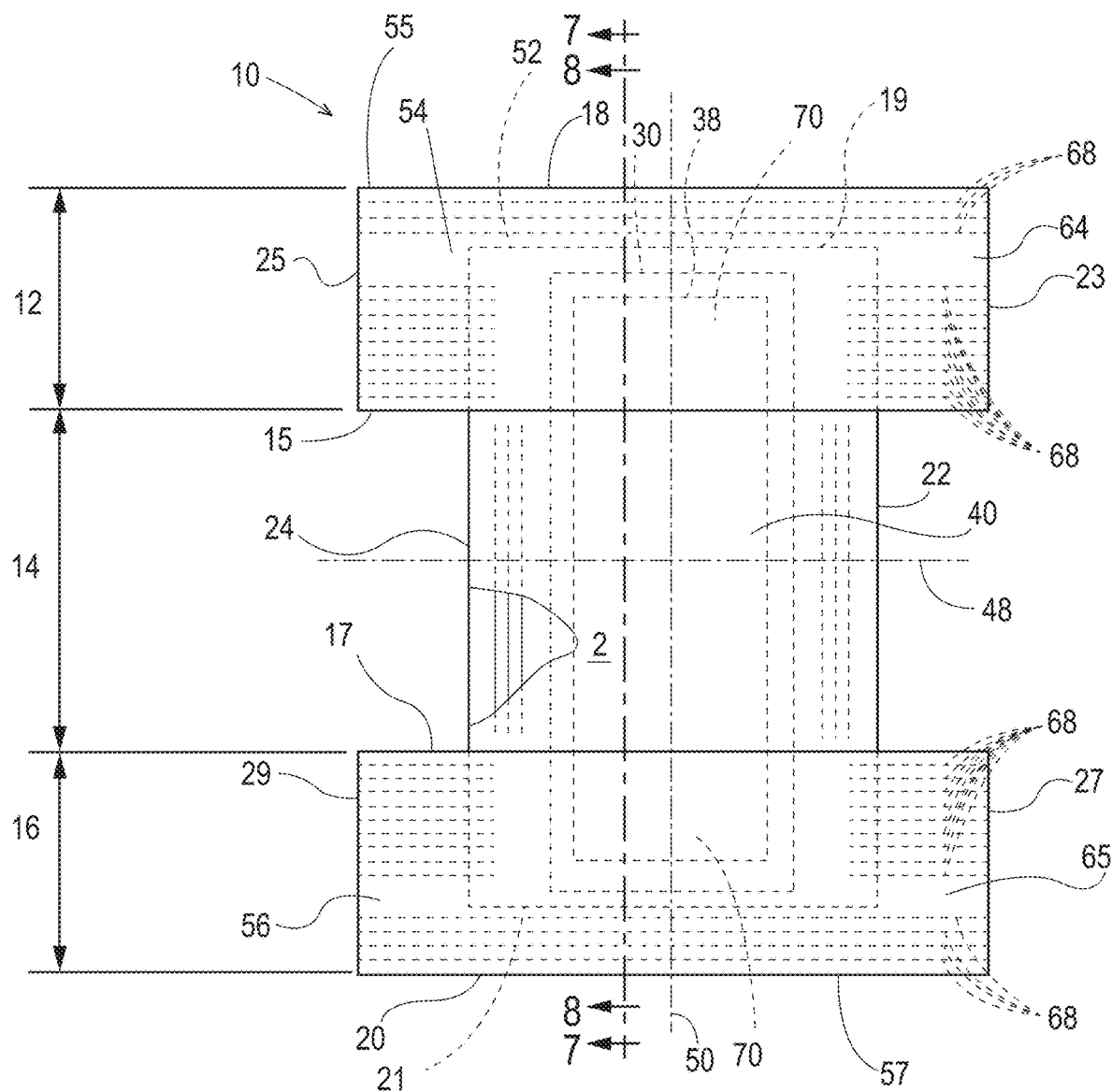
FIG. 6 is a plan view of the absorbent article of FIG. 4, laid flat, with a garment-facing surface facing the viewer.
Figure 7:
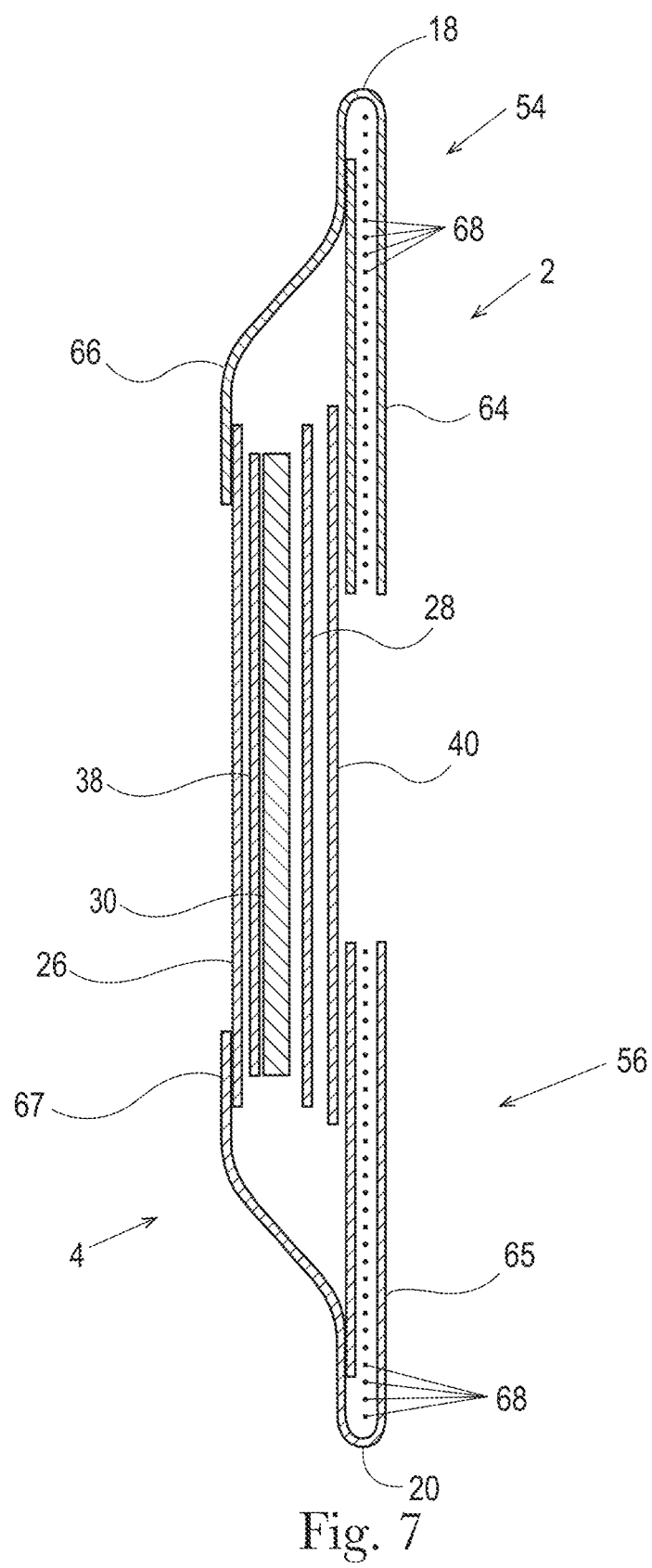
FIG. 7 is a cross-sectional view of the absorbent article taken about line 7-7 of FIG. 6.
Figure 8:
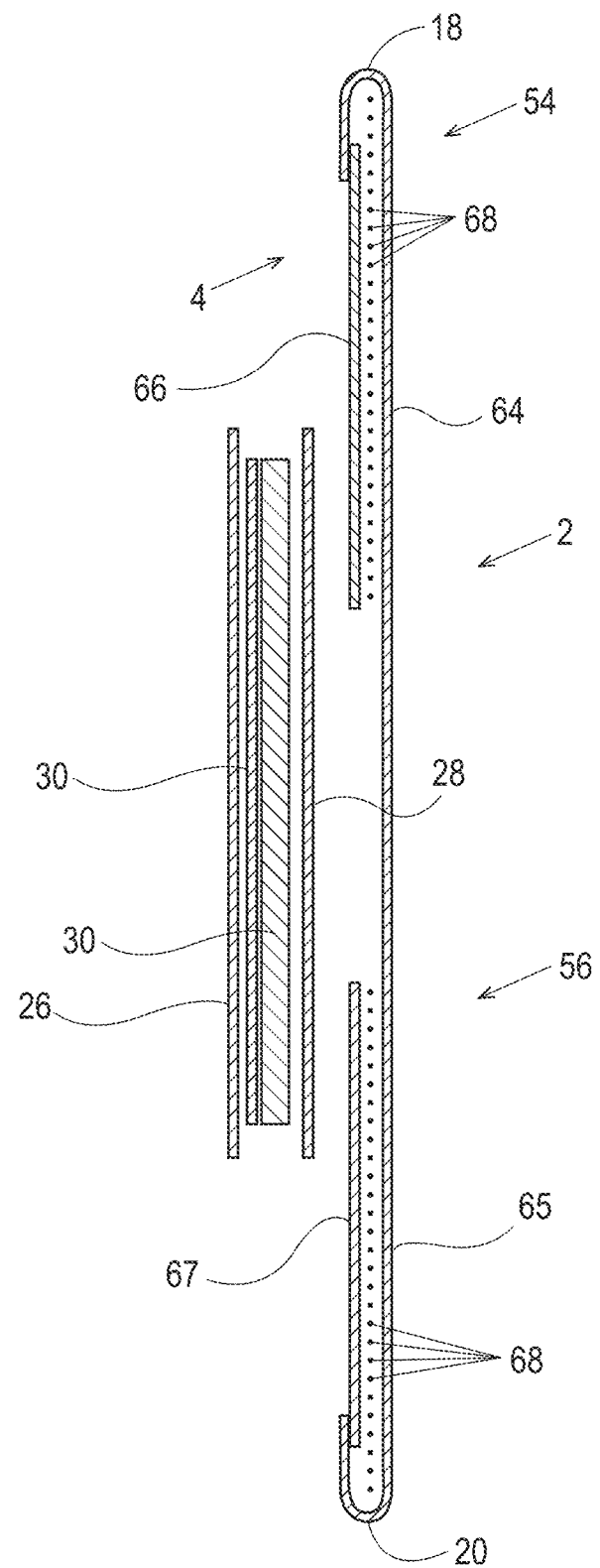
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from continuous fibers (e.g., spunbond), carded fibers, cotton fibers, other natural fibers, for example. The topsheet may comprise through-air bonded nonwoven materials. Some topsheets are apertured (FIG. 2, element 27).

The topsheet may comprise one of the webs discussed herein or may form a portion of the laminate for an absorbent article in combination with another layer for example. In some forms, the topsheet may form a single layer as discussed herein.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional elements. The outer cover material may comprise the webs discussed herein.

Absorbent Core

Figure 9:
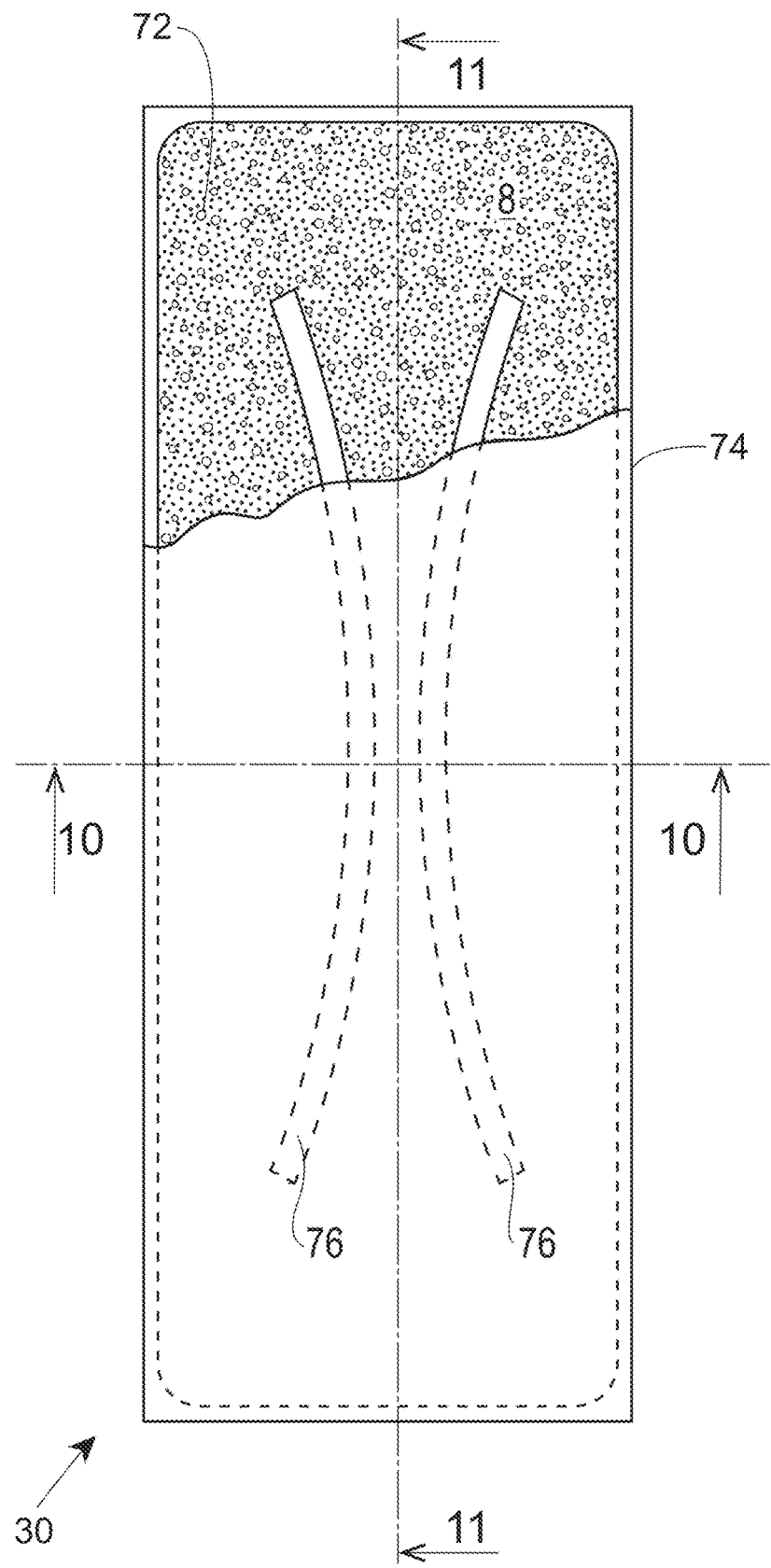
FIG. 9 is a plan view of an example absorbent core or an absorbent article.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package.

Sanitary Napkin

Figure 12:
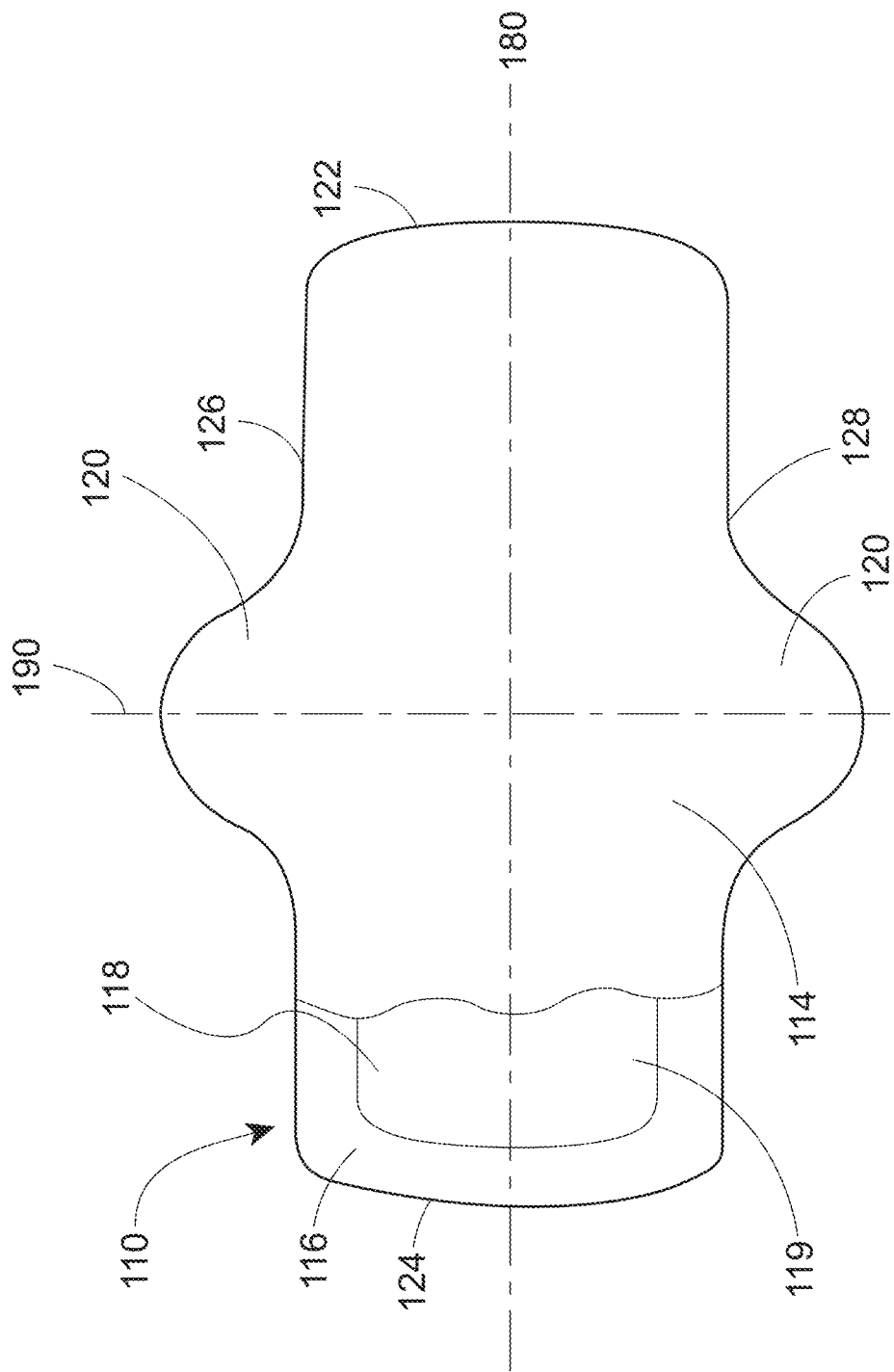
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

Examples Cross-Sectional Views of Absorbent Articles

Figure 13:
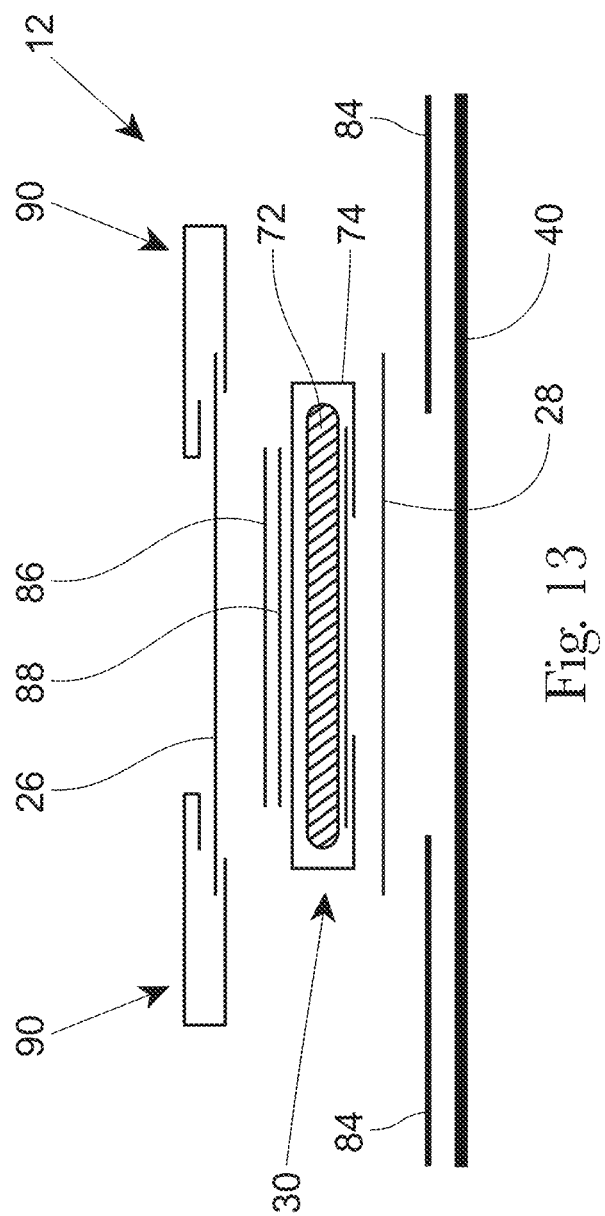
FIG. 13 is an example cross-sectional view taken within a front waist region of an absorbent article.
Figure 14:
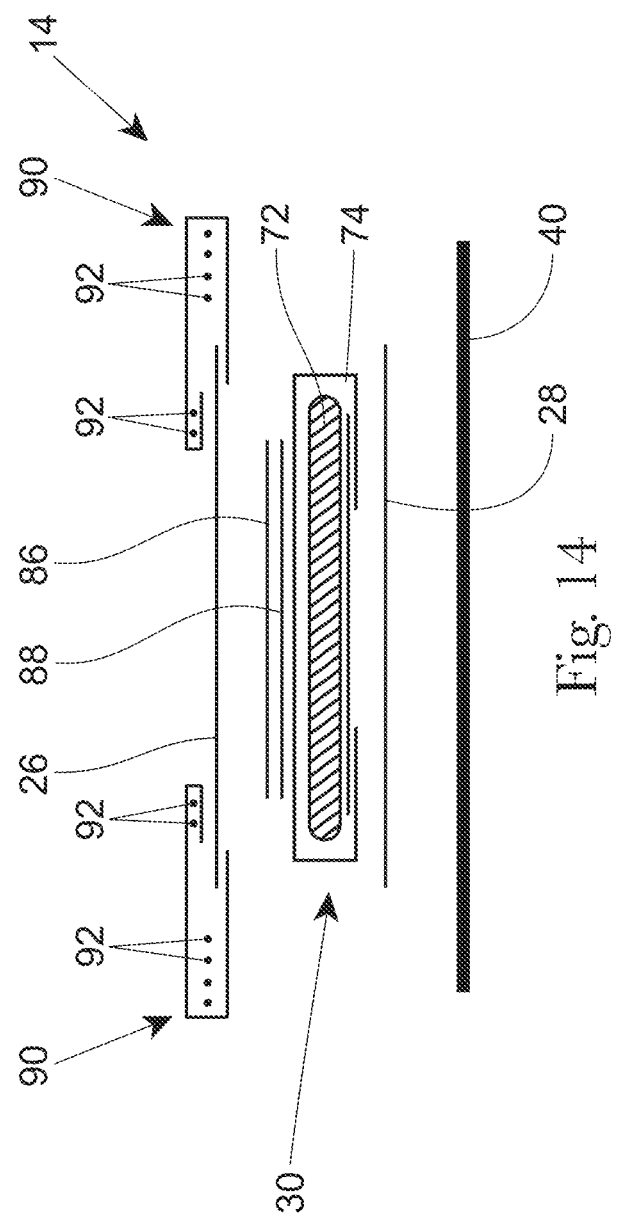
FIG. 14 is an example cross-sectional view taken within a crotch region of an absorbent article.
Figure 15:
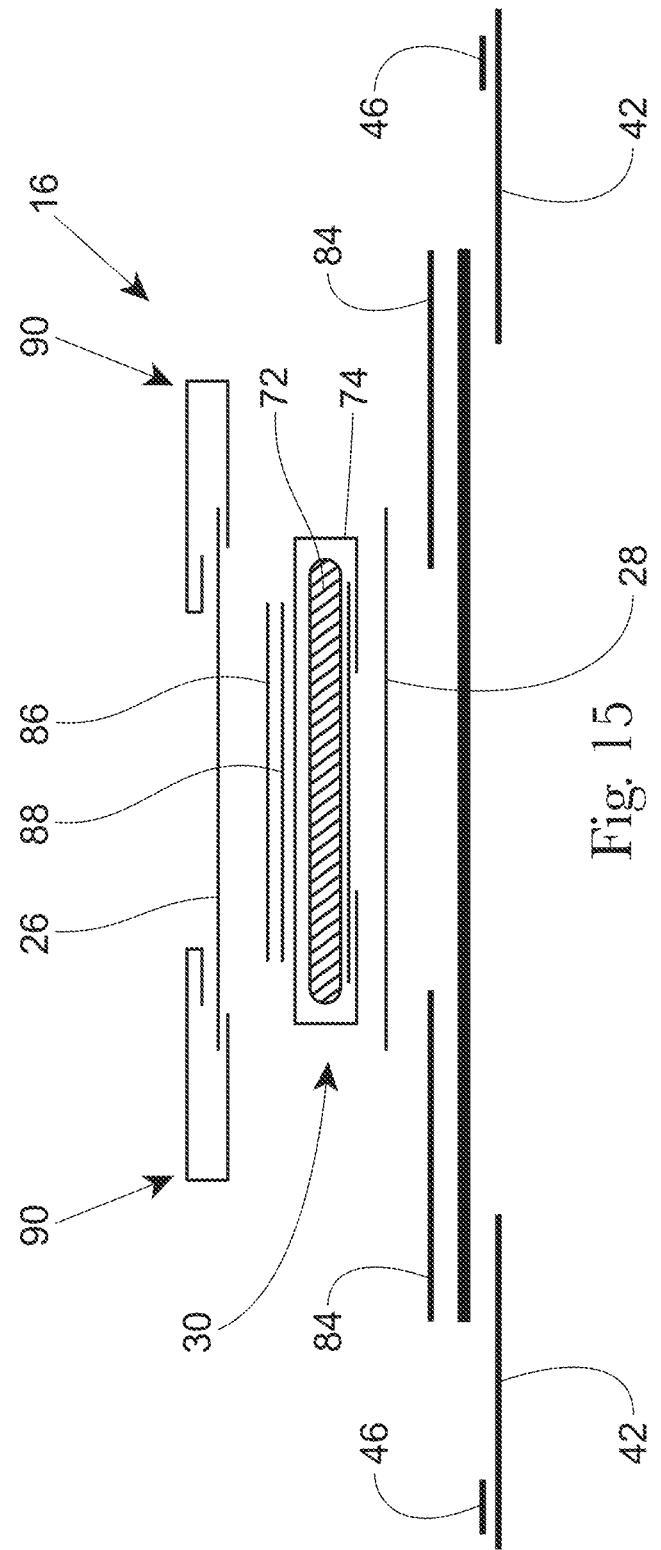
FIG. 15 is an example cross-sectional view taken within a back waist region of an absorbent article.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Webs or Topsheets for Absorbent Articles

Webs or topsheets for absorbent articles or other consumer products are provided herein. The absorbent articles discussed herein may comprise the webs as a topsheet, an acquisition material, a distribution material, a secondary topsheet, a core cover, an outer cover nonwoven, a portion of an elastic belt, and/or other components, for example. The webs or topsheets discussed herein may form a single layer web but may be joined with one or more materials to form a laminate. The one or more materials joined with the topsheet or web may comprise nonwoven material or films. The webs may also be used as wipes, cleaning or dusting substrates, or in other consumer products that comprise nonwoven materials. In some instances, the webs or topsheets may comprise wet-laid nonwoven materials, air-laid nonwoven materials, through-air bonded nonwoven materials, meltblown nonwoven materials, nano-fiber nonwoven materials, spunbond nonwoven materials, carded (staple fiber) nonwoven materials, spunlace nonwoven materials, or combinations of the same. The webs or topsheets may comprise synthetic and/or natural fibers. The natural fibers may comprise cotton, pulp, and/or bamboo, for example.

Figure 16:
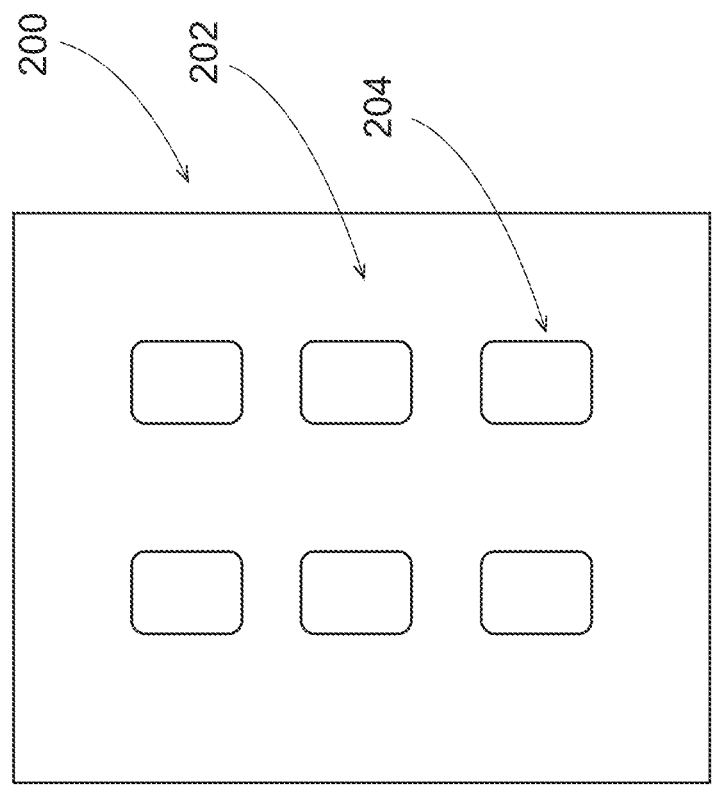
FIG. 16 is a plan view of a web or topsheet of the present disclosure having a continuous land area and discrete zones of modified surface energy in the form of bonds.

Referring to FIG. 16, the webs or topsheets 200 may comprise a continuous land area 202 or a plurality of discrete land areas. The webs or topsheets 200 may also comprise a plurality of discrete zones of modified surface energy 204. The discrete zones of modified surface energy 204 may have a different surface energy than the continuous land area. For example, if the continuous land area is hydrophobic, the discrete zones of modified surface energy may be hydrophilic or vice versa. As another example, if the continuous land area is hydrophilic, the discrete zone of modified surface energy may be more hydrophilic or vice versa. As yet another example, if the continuous land area is hydrophobic, the discrete zone of modified surface energy may be less hydrophobic or vice versa. The discrete zones of modified surface energy may comprise or form increased permeability regions that acquire bodily exudates faster than the continuous land area. The discrete zones of modified surface energy 204 may comprise bonds or be formed by bonds in the webs or topsheets 200. The bonds may be calendar or point bonds, overbonds, or other types of bonds, such as ultrasonic bonds.

Figure 17:
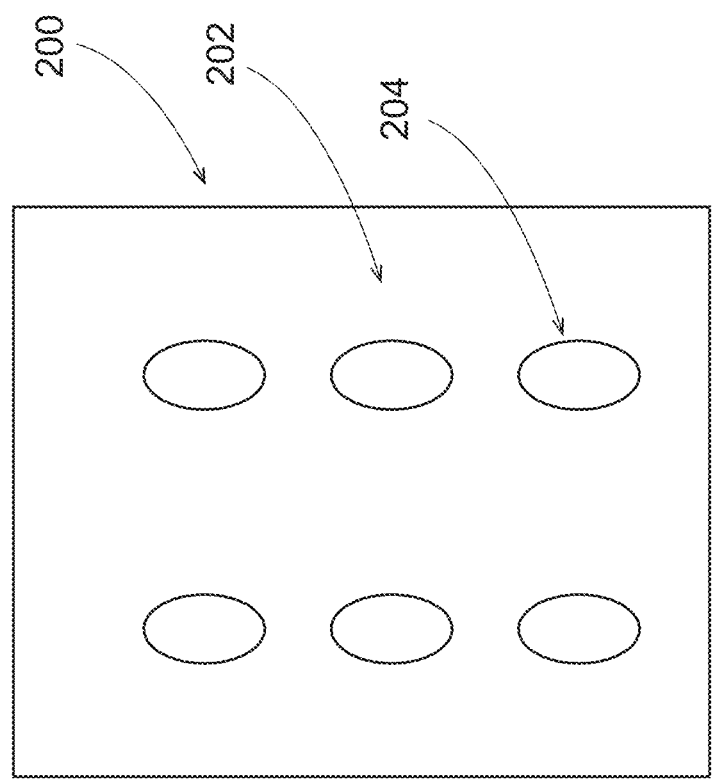
FIG. 17 is a plan view of a web or topsheet of the present disclosure having a continuous land area and discrete zones of modified surface energy in the form of perimeters of apertures and/or area adjacent to the apertures.

Referring to FIG. 17, the discrete zones of modified surface energy 204 may also be formed by bonds ruptured to form apertures or merely by aperturing, such as pin aperturing. As a result, perimeters of the apertures, partial perimeters of the apertures, and/or areas around the perimeters may comprise the discrete zones 204. In some forms, the discrete zones of modified surface energy 204 are not formed by applying a topical surface energy modifying treatment or by printing a surface energy modifying agent or treatment. Further, in some forms, the discrete zones of modified surface energy do not comprise topical surface energy modifying treatments. The discrete zones of modified surface energy 204 may take on any suitable pattern, shape, and/or size. As an example, the discrete zones 204 may be uniform in size, shape, and/or spacing therebetween or non-uniform in size, shape, and/or spacing therebetween. The discrete zones 204 may be formed in patterns or arrays or may be uniform throughout a web or topsheet. Any suitable number of discrete zones 204 may be formed in a topsheet or web.

The webs or topsheets may comprise a plurality of fibers. The fibers may comprise (or be formed only by) bicomponent fibers or fibers comprising more than two components (e.g., tricomponent fibers). Bicomponent fibers will be discussed herein, but it will be understood that tricomponent fibers may also be used in a similar fashion. Referring to FIG. 18, an example side view of a bicomponent fiber 206 is illustrated. The bicomponent fiber 206 may comprise a spunbond bicomponent fiber, a carded bicomponent fibers, a micro-fiber bicomponent fiber, a nano-fiber bicomponent fiber, a meltblown bicomponent fiber, or a bicomponent fiber comprising one or more natural components or bio-sourced components, for example. The fibers may have a round or non-round cross-section. As used herein, the term "non-round fiber(s)" describes fibers having a non-round cross-section, and comprises "shaped fibers" and "capillary channel fibers." Such fibers may be solid or hollow, and the fibers may be tri-lobal, delta-shaped, and may comprise fibers having capillary channels on their outer surfaces. The capillary channels may be of various cross-sectional shapes such as "U-shaped", "H-shaped", "C-shaped" and "V-shaped". The fibers may be round, hollow, or shaped, such as tri-lobal, ribbon, capillary channel fibers (e.g., 4DG). The bicomponent fibers may be any of the following types of bicomponent fibers, such as PP/PE, PET/PE, PET/coPET, or PLA/PE, for example. The bicomponent fibers may also comprise bio-sourced materials, natural material, or blends of the same.

The bicomponent fibers may have a concentric or eccentric core/sheath configuration, an islands-in-the-sea configuration, a side-by-side configuration, and/or any other suitable bicomponent fiber configurations where at least a portion of a surface of the fibers comprises a lower melting component, for example. The bicomponent fibers may be blended with other fibers that are monocomponent fibers to form a topsheet or a web so that the topsheet or the web is formed at least partially by bicomponent fibers.

The bicomponent fibers may each have a first component and a second component. At least some of, or all of, the first components (outer component) may comprise a hydrophobic resin and/or a hydrophobic melt additive. At least some of, or all of, the second components (inner component) may comprise hydrophilic resin and/or a hydrophilic melt additive. Typically, the first component will surround the second component until heat, pressure, and/or energy is provided to the precursor web or topsheet. In such an instance, the second component may only be exposed in the discrete zones 204 thereby rendering the discrete zones hydrophilic and maintaining the continuous land area 202 hydrophobic or rendering the discrete zones to have a different hydrophilicity than the continuous land area. Alternatively, the second component may surround the first component. In such an instance, the first component may only be exposed in the discrete zones 204 rendering the discrete zones hydrophobic and maintaining the continuous land area 202 hydrophilic or rendering the discrete zones to have a different hydrophilicity than the continuous land area.

Any suitable hydrophilic melt additives may be used in the bicomponent fibers to form the first or second components (depending on the desired configuration of the fibers). Examples include those available from Techmer PM, Clinton, Tennessee, USA sold under the trade name of Techmer PPM15560; TPM12713, PPM19913, PPM 19441, PPM19914, PPM112221 (for polypropylene), and/or PM19668, PM112222 (for polyethylene). Additional examples are available from Polyvel Inc. located in Hammonton, New Jersey, USA, sold under the trade name of Polyvel VW351 PP Wetting Agent (for polypropylene); from Goulston Technologies Inc. located in Monroe, North Carolina, USA sold under the trade name Hydrosorb 1001; as well as those hydrophilic additives disclosed in U.S. Patent Application Publication No. 2012/0077886 and U.S. Pat. Nos. 5,969,026 and 4,578,414.

Some polymers like PET may be made inherently hydrophilic by incorporation of hydrophilic comonomers into the polymer chain. Polylactic acid can be effectively rendered hydrophilic by using the melt additives such as Unithox 750 (with additional tempering), Pluronic F68, Pluronic F88, and Pluronic F108. This may be a further form of providing a hydrophilic second component in a bicomponent fiber.

Any suitable hydrophobic melt additives may be used in the bicomponent fibers to form the first or second components (depending on the desired configuration of the fibers). Some examples of hydrophobic melt additives are glycerol tristearate (GTS) and Erucamide. Other examples of hydrophobic melt additives may comprise fatty acids and fatty acid derivatives. The fatty acids may originate from vegetable, animal, and/or synthetic sources. Some fatty acids may range from a C8 fatty acid to a C30 fatty acid, or from a C12 fatty acid to a C22 fatty acid. In other forms, a substantially saturated fatty acid may be used, particularly when saturation arises as a result of hydrogenation of fatty acid precursor. Examples of fatty acid derivatives include fatty alcohols, fatty acid esters, and fatty acid amides. Suitable fatty alcohols (R—OH) include those derived from C12-C28 fatty acids.

Without being bound by theory, it is believed that having a hydrophobic resin or melt additive in a sheath or sea of a bicomponent fiber may help to retard the migration of a hydrophilic resin or melt additive in a core or islands of the bicomponent fiber.

Further details regarding the hydrophilic and hydrophobic melt additives are disclosed in U.S. Patent Appl. Publ. No. 2017/0258651, to Hammons et al., published on Sep. 14, 2017.

Figure 19:
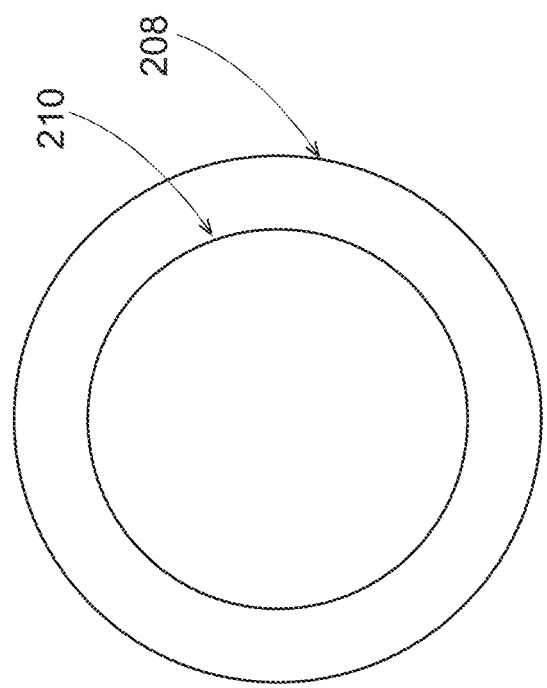
FIG. 19 is an example cross-sectional illustration taken about line 19-19 of FIG. 18 of a core/sheath bicomponent fiber prior to heat and/or energy being applied to the bicomponent fiber.

FIG. 19 is an example cross-sectional view of the fiber 206 taken about line 19-19 of FIG. 18 illustrating a concentric core/sheath bicomponent fiber. The sheath may be formed by a first component 208 and the core may be formed by a second component 210. The first component 208 may comprise a hydrophobic resin and/or a hydrophobic melt additive and the second component 210 may comprise a hydrophilic resin and/or a hydrophilic melt additive.

Figure 20:
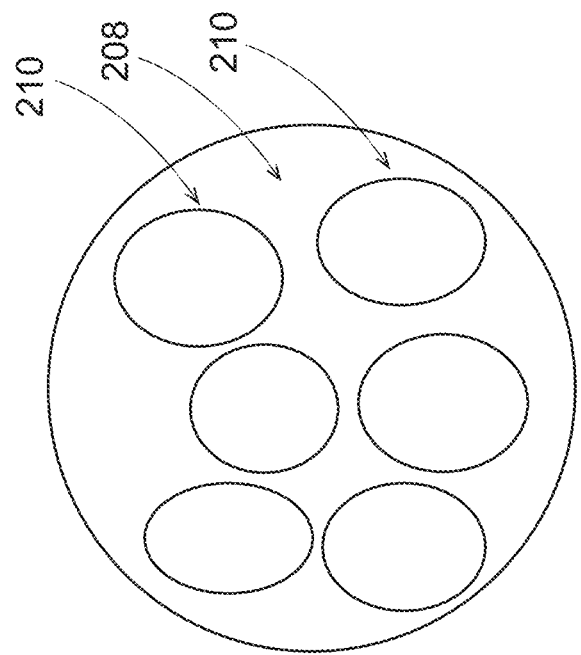
FIG. 20 is another example cross-sectional illustration taken about line 19-19 of FIG. 18 of an islands-is-the-sea bicomponent fiber prior to heat and/or energy being applied to the bicomponent fiber.

FIG. 20 is an example cross-sectional view of the fiber 206 taken about line 19-19 of FIG. 18 illustrating an islands-in-the-sea bicomponent fiber. The sea may be formed by a first component 208 and the islands may be formed by a second component 210. The islands may take on any suitable shape, such as circular, elliptical, and/or ovate, for example. The first component 208 may comprise a hydrophobic resin and/or a hydrophobic melt additive and the second component 210 may comprise a hydrophilic resin and/or a hydrophilic melt additive.

Figure 21:
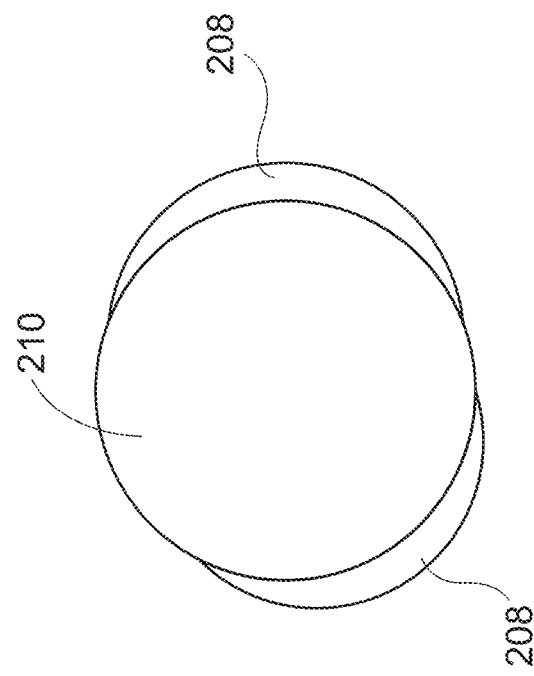
FIG. 21 is an example cross-sectional illustration of the bicomponent fiber of FIG. 19 after heat and/or energy are applied thereto.

FIG. 21 is an example cross-sectional view of the concentric core/sheath bicomponent fiber 206 of FIG. 19 in a discrete zone of modified surface energy (i.e., after heat and/or energy has been applied to the fiber). The sheath/first component 208 comprising the hydrophobic resin and/or hydrophobic melt additive may be partially or fully moved or melted away due to the energy/heat. As a result, the core/second component 210 comprising the hydrophilic resin and/or hydrophilic melt additive may be at least partially exposed, thereby rendering the discrete zone of modified surface energy hydrophilic or at least partially hydrophilic. In the continuous land area 202, where heat and/or energy are not applied to the web or topsheet, the sheath/first component 208 may not expose the core/second component 210, thereby maintaining the fibers in the continuous land area hydrophobic.

As an alternative to the sheath/sea/first components herein being partially or fully moved or melted away in a discrete zone of modified surface energy, the first and second components may be fused and/or blended together in the discrete zones when heat and/or energy is applied, thereby rendering the discrete zone to have a surface energy that is a blend of the first and second components. Stated another way, the discrete zones may have a surface energy intermediate a surface energy of the first component and a surface energy of the second component. This is not the result of the melt additive(s) spontaneously blooming, but occurs after any spontaneous blooming.

Figure 22:
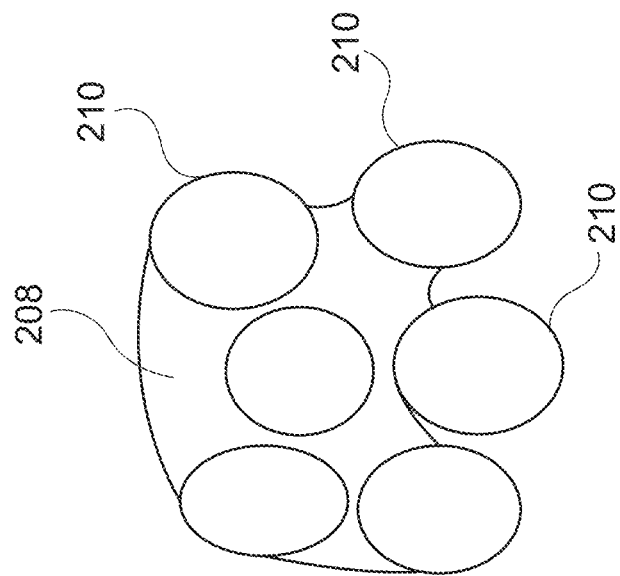
FIG. 22 is an example cross-sectional illustration of the bicomponent fiber of FIG. 20 after heat and/or energy are applied thereto.

FIG. 22 is an example cross-sectional view of the islands-in-the-sea bicomponent fiber 206 of FIG. 20 in a discrete zone of modified surface energy (i.e., after heat and/or energy has been applied to the fiber). The sea/first component 208 comprising the hydrophobic resin and/or hydrophobic melt additive may be partially or fully melted away due to the energy/heat. As a result, the islands/second component 210 comprising the hydrophilic resin and/or hydrophilic melt additive may be at least partially exposed, thereby rendering the discrete zone of modified surface energy hydrophilic or at least partially hydrophilic. In the continuous land area 202, where heat and/or energy are not applied to the web or topsheet, the sea/first component 208 may not expose the islands/second component 210, thereby maintaining the fibers in the continuous land area hydrophobic.

Figure 23:
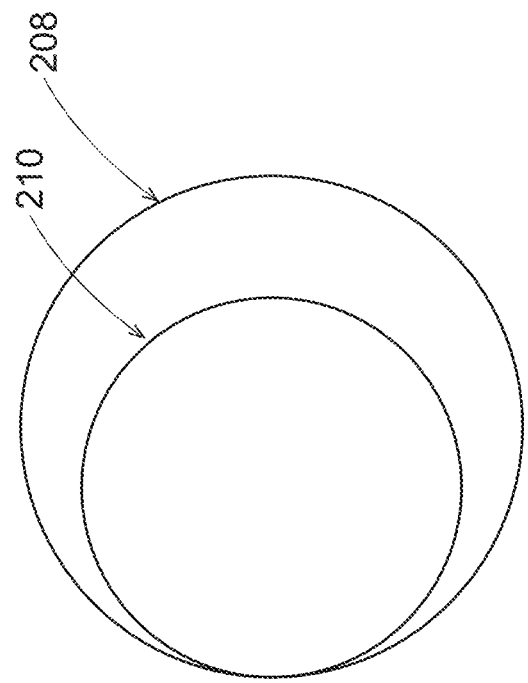
FIG. 23 is another example cross-sectional illustration taken about line 19-19 of FIG. 18 of an eccentric bicomponent fiber prior to heat and/or energy being applied to the bicomponent fiber.

FIG. 23 is an example cross-sectional view of the fiber 206 taken about line 19-19 of FIG. 18 illustrating an eccentric core/sheath bicomponent fiber. The sheath may be formed by a first component 208 and the core may be formed by a second component 210. The first component 208 may comprise a hydrophobic resin and/or a hydrophobic melt additive and the second component 210 may comprise a hydrophilic resin and/or hydrophilic melt additive. In order to expose the hydrophilic second component or core of the bicomponent fiber only by heat, an eccentric core/sheath bicomponent geometry may be advantageous in that it may enable the first component or sheath to easily flow away on one side (since it is thinner), further aided by the incompatibility of core and sheath.

Different measures may be taken to further increase the flowing tendency of the sheath of a bicomponent fiber. In through-air bonding, for example, the sheath is typically a polymer of lower melting point than the core (e.g., a PE in the sheath versus PP or PET in the core). The use of grades of polymers with lower molecular weights for the sheath may help to further increase the flow rate of the sheath.

Figure 24:
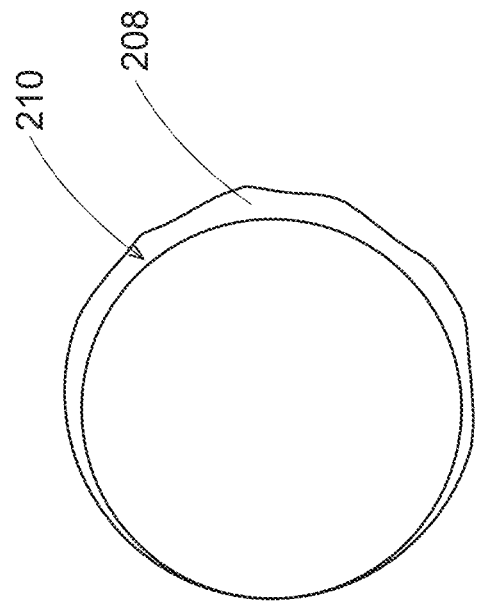
FIG. 24 is an example cross-sectional illustration of the bicomponent fiber of FIG. 23 after heat and/or energy are applied thereto.

FIG. 24 is an example cross-sectional view of the eccentric core/sheath bicomponent fiber 206 of FIG. 23 in a discrete zone of modified surface energy (i.e., after heat and/or energy has been applied to the fiber). The sheath/first component 208 comprising the hydrophobic resin and/or the hydrophobic melt additive may be partially or fully melted away due to the energy and/or heat. As a result, the core/second component 210 comprising the hydrophilic resin or hydrophilic melt additive may be at least partially exposed, thereby rendering the discrete zone of modified surface energy hydrophilic or at least partially hydrophilic. In the continuous land area 202, where heat and/or energy are not applied to the web or topsheet, the sheath/first component 208 may not expose the core/second component 210, thereby maintaining the fibers in the continuous land area hydrophobic. Eccentric core/sheath bicomponent fibers may be desired for the present disclosure in that the core/second component 210 is already proximate to an outer surface of the fiber prior to heat and/or energy being applied to the fibers in the discrete zones. As a result, it may require less heat and/or energy to expose the core/second component 210 of an eccentric fiber and render the fiber at least partially hydrophilic on its outer surface.

Figure 25:
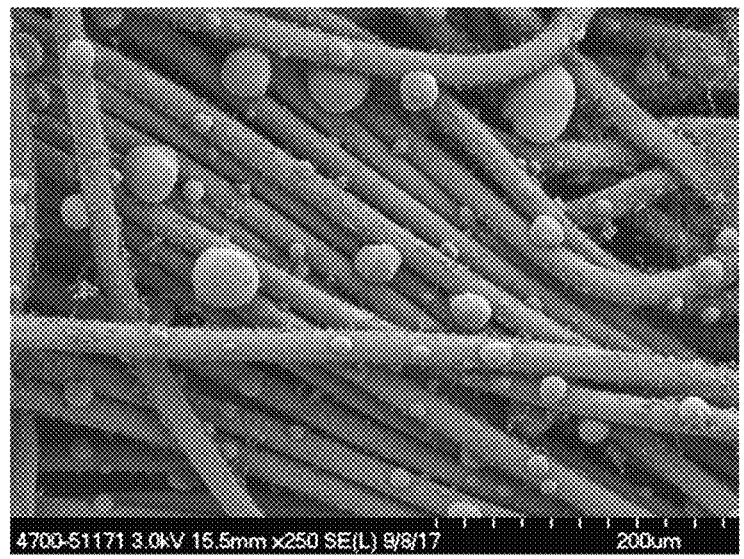
FIG. 25 is a microscope image of some fibers of a continuous land area with water droplets applied thereto.
Figure 26:
FIG. 26 is a further magnified view of the fibers of the continuous land area of FIG. 25.

FIG. 25 is a microscope image of some fibers of a continuous land area 202 of a web or topsheet comprising concentric core/sheath bicomponent fibers after having droplets of water applied thereto, according to the Contact Angle Test herein. FIG. 26 is a further magnified view of the fibers of the continuous land area 202 of FIG. 25. The sheath/first component 208 (see FIG. 19) comprises a hydrophobic resin or a hydrophobic melt additive. The core/second component 210 (see FIG. 19) comprises a hydrophilic resin or a hydrophilic melt additive. In the continuous land area 202, the core/second component 210 is not exposed to maintain the continuous land area hydrophobic. The measured contact angle with water in the sample illustrated in FIGS. 25 and 26 was 110.1 degrees+/−10.9 degrees, according to the Contact Angle Test herein. Therefore, the bicomponent fibers in the continuous land area maintain their hydrophobic character.

Figure 27:
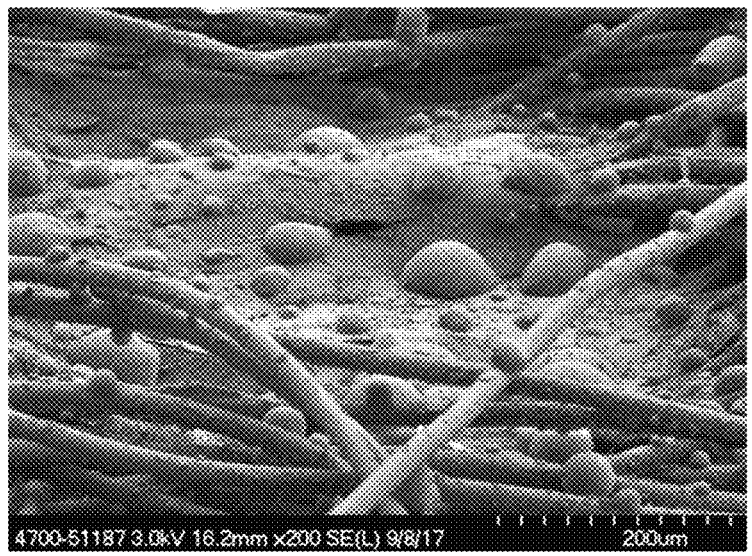
FIG. 27 is a microscope image of some fibers of a calendar bond with water droplets applied thereto.
Figure 28:
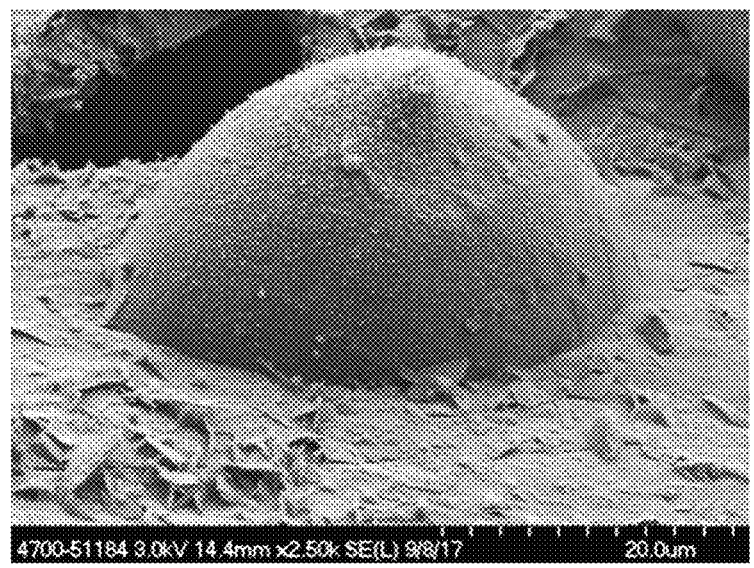
FIG. 28 is a further magnified view of the fibers of the calendar bond of FIG. 27.

FIG. 27 is a microscope image of some fibers of a calendar bond of a discrete zone of modified surface energy comprising concentric core/sheath bicomponent fibers after having droplets of water applied thereto, according to the Contact Angle Test herein. FIG. 28 is a further magnified view of the fibers of the calendar bond of FIG. 27. The sheath/first component 208 (see FIG. 19) comprises a hydrophobic resin or a hydrophobic melt additive. The core/second component 210 (see FIG. 19) comprises a hydrophilic resin or a hydrophilic melt additive. In the overbond, the core/second component 210 is exposed to render the overbond (discrete zone) hydrophilic. The measured contact angle in the sample illustrated in FIGS. 27 and 28 was 72.3 degrees+/−8.39 degrees, according to the Contract Angle Test herein. Therefore, the bicomponent fibers in the overbond (or discrete zone of modified surface energy) are rendered hydrophilic.

Figure 29:
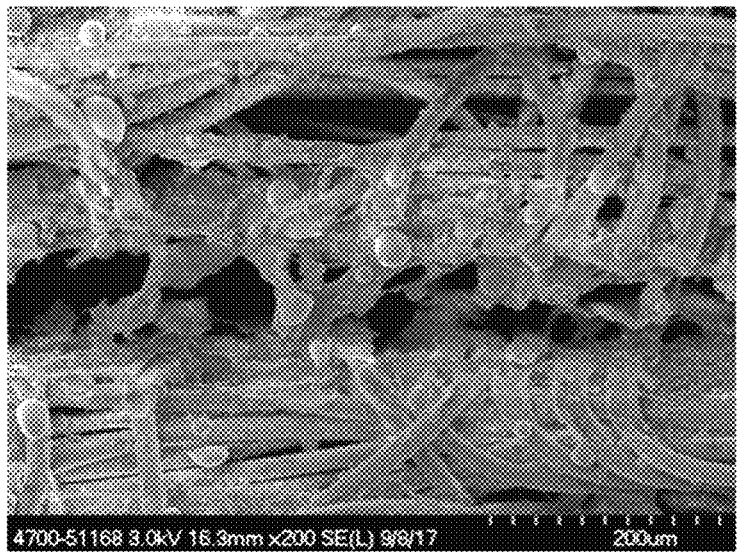
FIG. 29 is a microscope image of fibers in a portion of an overbond.
Figure 30:
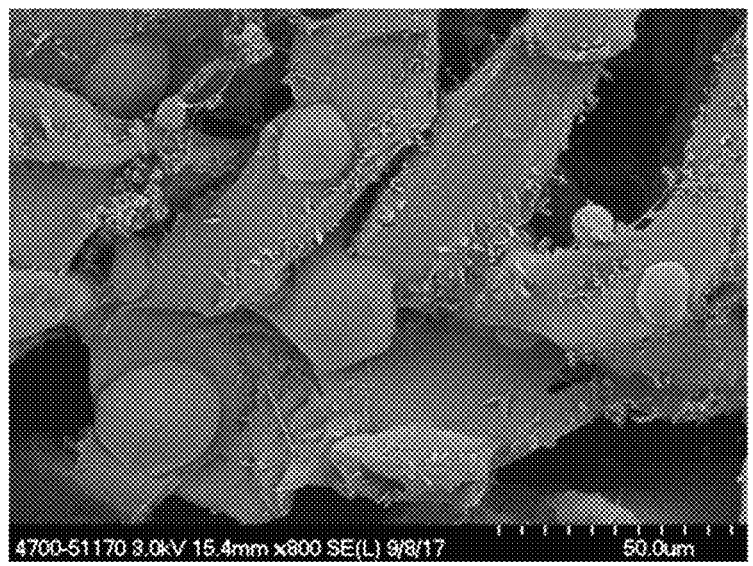
FIG. 30 is a further magnified view of the fiber of the portion of the overbond of FIG. 29.

FIG. 29 is a microscope image of some fibers of a portion of an overbond. The overbond may be considered a discrete zone of modified surface energy. The overbond has droplets of water applied thereto, according to the Contact Angle Test therein. FIG. 30 is a further magnified view of the fibers of the portion of the overbond of FIG. 29. As can be seen from the water droplets, the bicomponent fibers in overbond are rendered hydrophilic since the contact angle between the fibers and the droplets of the water are less than 90 degrees. On information and belief, the contact angle on the fibers of the overbond may be lower than the fibers of the continuous land area of FIGS. 25 and 26 and lower than the contact angle of the fibers in the calendar bond of FIGS. 27 and 28.

Figure 30A:
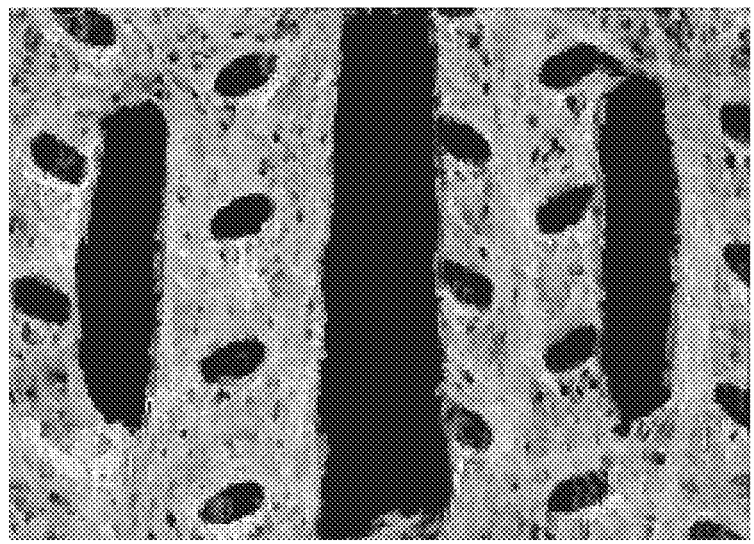
FIG. 30A is a microscope image of melt rims around apertures, wherein the apertures were created by cross-directionally stretching overbonds, such as the overbond of FIGS. 29 and 30.

FIG. 30A is a microscope image of melt rims 220 around apertures 222, wherein the apertures 222 were created by cross-directionally stretching an overbond. The melt rims 22 may have the same or similar contact angle as the overbonds of FIGS. 29 and 30.

FIGS. 25-30A are images of a spunbond web with a basis weight of 25 gsm. The spunbond web was produced using approximately 20 micron diameter sheath/core bicomponent fibers. The sheath was polyethylene (Dow Aspun™ 6850A) and a hydrophobic masterbatch comprising glyceryl tristearate. The core was polypropylene (Exxon Mobile PP3155), $TiO_2$, and a hydrophilic masterbatch (PPM15560 from Techmer). Overbonds were created by running the nonwoven webs between a heated anvil roll and a pattern roll at 900 ft/min at conditions sufficient to generate flow in the polymers. Contact angles were measured according to the Contact Angle Test herein.

Figure 31:
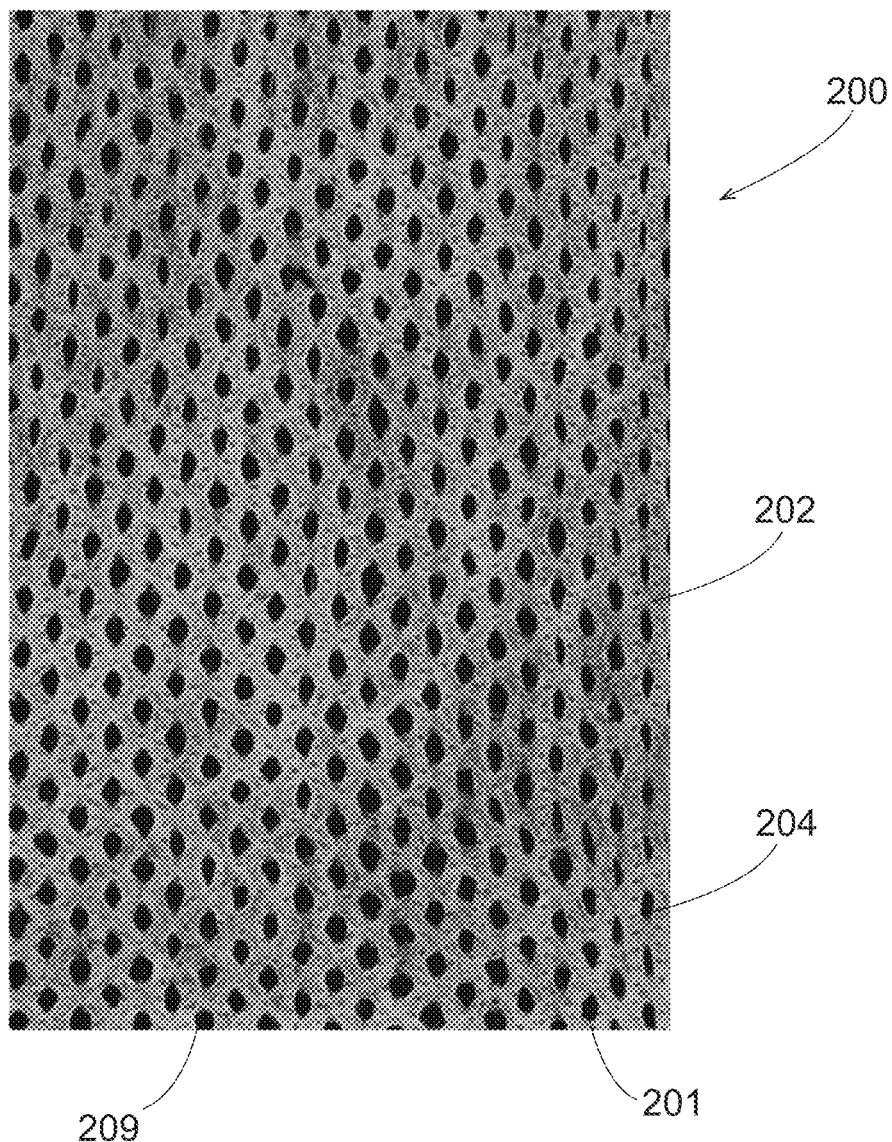
FIG. 31 is photograph of a web or topsheet having uniform and homogeneous apertures.

FIG. 31 is an example of a portion of topsheet or web 200 having a continuous land area 202 and discrete zones of modified surface energy 204. The topsheet or web 200 has a pattern of what is considered a uniform and homogeneous pattern of apertures (intended to be uniform and homogenous). Each of the apertures 201 has a perimeter. The discrete zones of modified surface energy 204 are formed in and/or proximate to at least some of, or all of, the aperture perimeters. The discrete zones may also be formed partially around perimeters of the apertures.

Figure 32:
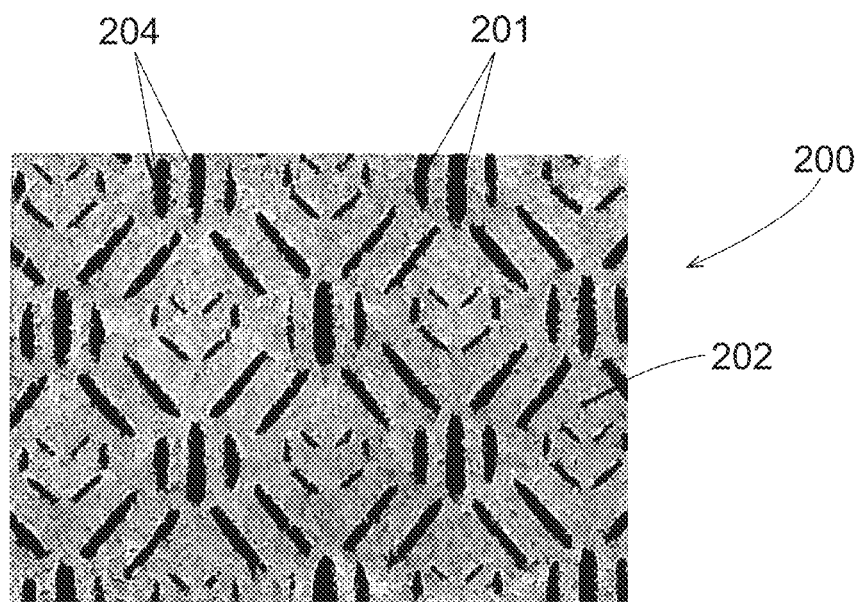
FIG. 32 is a photograph of a web or topsheet having non-uniform and non-homogeneous apertures.

FIG. 32 is an example of a portion of a topsheet or web 200 having a continuous land area 202 and discrete zones of modified surface energy 204. The topsheet or web 200 has a pattern of what is considered non-uniform and nonhomogeneous apertures 201. Each of the apertures 201 has a perimeter. The discrete zones of modified surface energy 204 are formed in and/or proximate to at least some of, or all of, the aperture perimeters. The discrete zones may also be formed partially around perimeters of the apertures 201.

Figure 33:
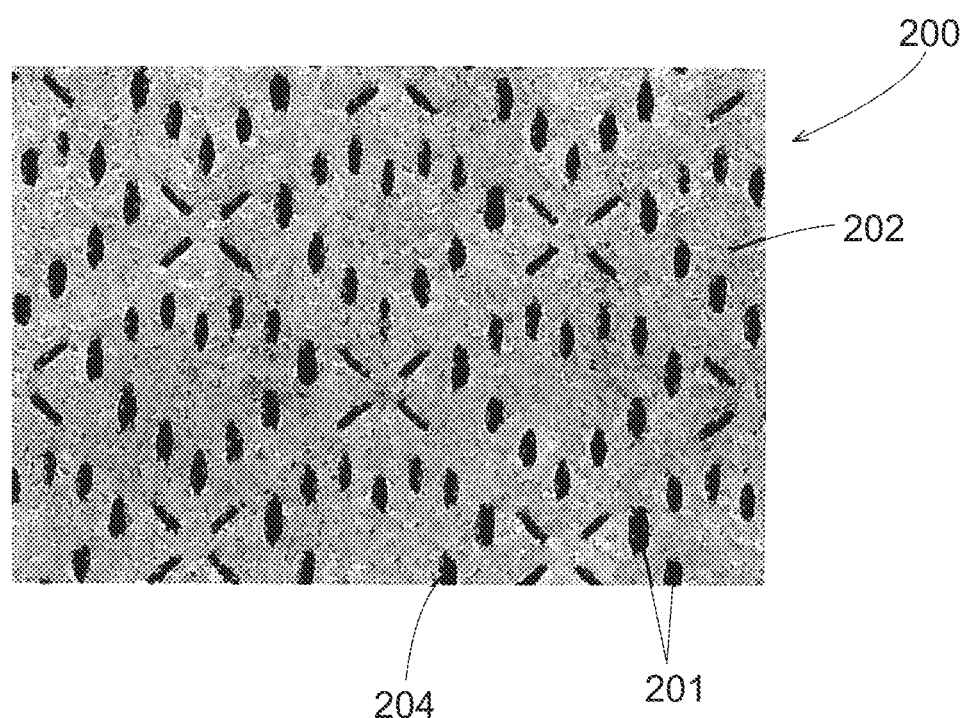
FIG. 33 is a photograph of a web or topsheet having non-uniform and non-homogeneous apertures.

FIG. 33 is another example of a portion of a topsheet or web 200 having a continuous land area 202 and discrete zones of modified surface energy 204. The topsheet or web 200 has a pattern of what is considered non-uniform and nonhomogeneous apertures 201. Each of the apertures 201 has a perimeter. The discrete zones of modified surface energy 204 are formed in and/or proximate to at least some of, or all of, the aperture perimeters. The discrete zones may also be formed partially around perimeters of the apertures 201.

FIGS. 31-33 show some example aperture patterns, but the present disclosure is not limited to such patterns and may have any suitable patterns tailored for a certain intended purpose.

The basis weight of webs or topsheets of the present disclosure may vary according to the intended purpose of the webs or topsheets. The basis weight of the webs or topsheets may be in the range of about 10 gsm (grams per square meter) to about 80 gsm, about 10 gsm to about 60 gsm, about 10 gsm to about 50 gsm, about 10 gsm to about 40 gsm, about 10 gsm to about 35 gsm, about 10 gsm to about 30 gsm, about 10 gsm to about 25 gsm, or about 10 gsm to about 20 gsm, specifically reciting all 0.1 gsm increments within the specified ranges and all ranges formed therein or thereby.

The webs or topsheets discussed herein may have the same color or different colors than other webs or layers in an absorbent article or other consumer product. In some instances, a web or topsheet may be a first, non-white color, and a second material may be white or may be a second non-white color. As an example, a web or topsheet may be white and the second material may be teal, or vice versa. As another example, a web or topsheet may be teal and the second nonwoven material may be blue, or vice versa.

Figure 34:
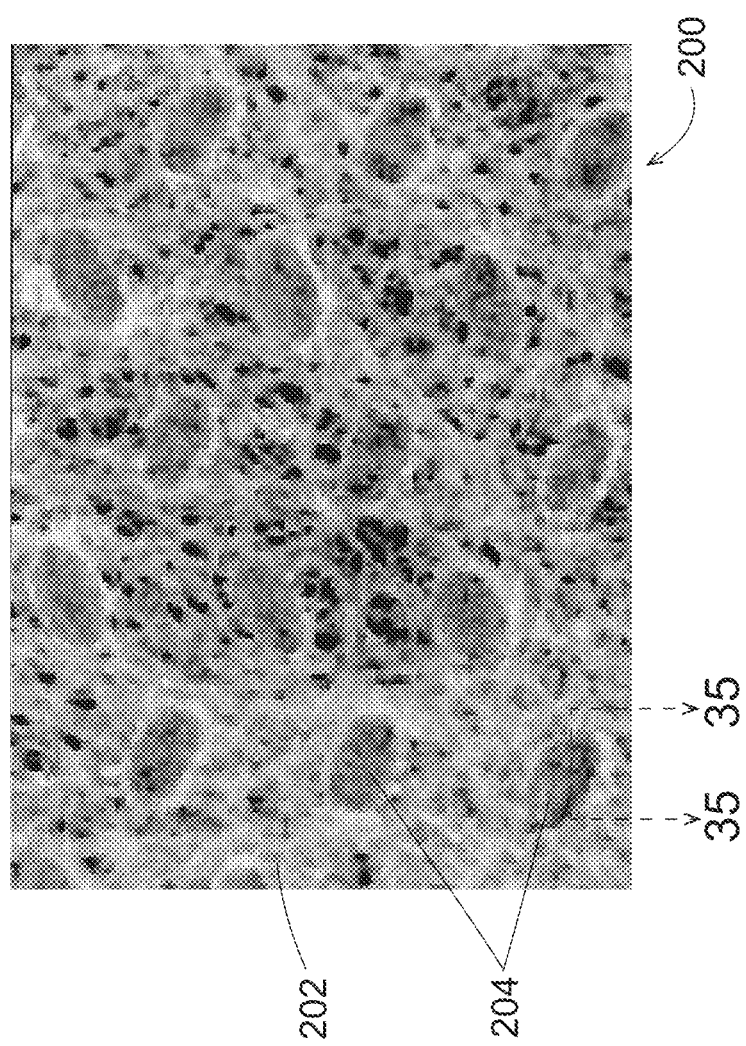
FIG. 34 is a top view photograph of a calendar or point bonded topsheet or web.
Figure 35:
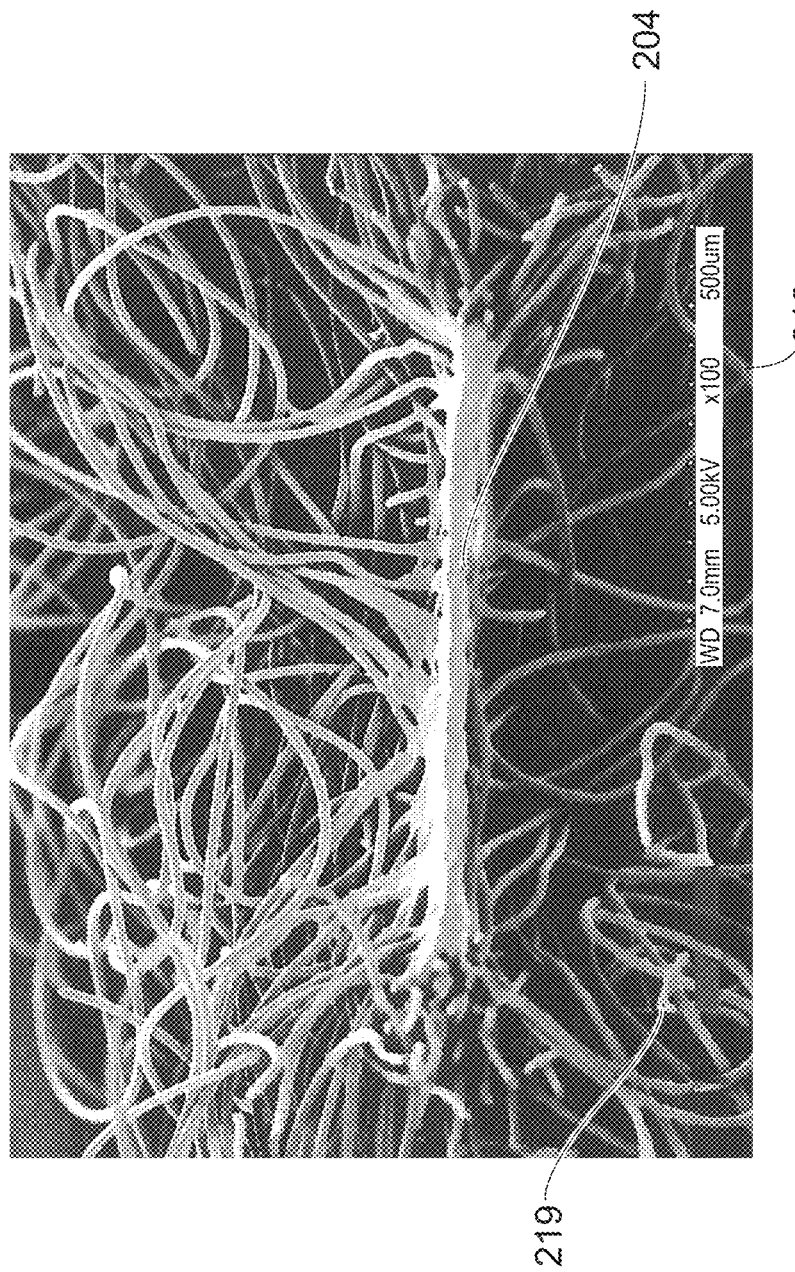
FIG. 35 is a cross-sectional photograph taken about line 35-35 of FIG. 34 and illustrating a calendar or point bond.

FIG. 34 illustrates a top view photograph of a portion of a web or topsheet comprising calendar or point bonds that form discrete zones of modified surface energy 204. The web or topsheet 200 of FIG. 34 also illustrates a continuous land area 202. The web or topsheet comprises bicomponent fibers having a first component and a second component as discussed herein. FIG. 35 is a cross-sectional schematic illustration taken about line 35-35 of FIG. 34. FIG. 35 illustrates a calendar or point bond that forms a discrete zone of modified surface energy 204 surrounded by unbonded fibers 219 in the continuous land area 202. The calendar or point bonds are essentially highly densified regions within the web or topsheet. These calendar or point bonds typically have uniform sizes, shapes, and are uniformly spaced relative to each other. The calendar or point bonds may be used during the nonwoven web manufacturing process to join some of the fibers 219 together to form the nonwoven webs and provide them with integrity. Typically, these calendar or point bonds are created by conveying the bicomponent fibers of the present disclosure through a nip between a calendar roll having plurality of nubs (that create the bonds) and an anvil roll, as is generally known in the art.

Methods of Making Apertured Webs and/or Topsheets

The apertured webs or topsheets of the present disclosure may be made generally by using the process generally described in U.S. Pat. No. 5,628,097 entitled "Method for Selectively Aperturing a Nonwoven Web", which issued on May 13, 1997 and U.S. Patent Publication 2003/0021951 entitled "High Elongation Apertured Nonwoven Web and Method of Making", published on Jan. 20, 2003. This process is described in further detail below. The apertured webs or topsheets may also be made by hydroforming carded webs, laser cutting, punching with a patterned roll, pin-aperturing, or other suitable aperturing methods.

Figure 36:
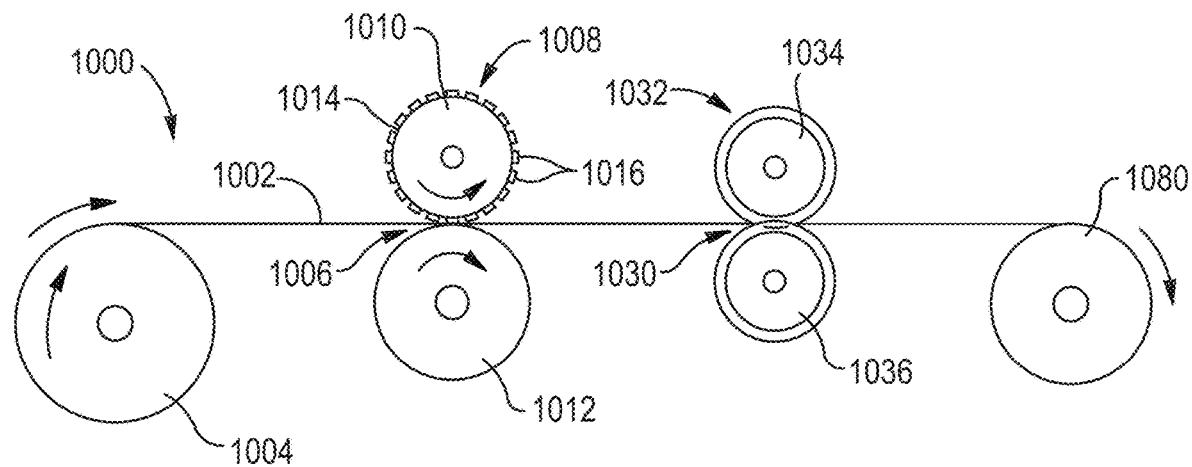
FIG. 36 is a schematic representation of an example process for producing apertured topsheets or webs of the present disclosure.

Referring to FIG. 36 there is schematically illustrated at 1000 one process for forming apertured webs or topsheets. First, a precursor material 1002 is supplied as the starting material. The precursor material 102 may be supplied as roll stock. The precursor material 1002 may be a single layer web, such as a single layer spunbond on continuous fiber web, having bicomponent fibers with a first component comprising a hydrophobic resin or a hydrophobic melt additive and with a second component comprising a hydrophilic resin or a hydrophilic melt additive or vice versa.

The precursor material 1002 may be unwound from a supply roll 1004 and travel in a direction indicated by the arrow associated therewith as the supply roll 1004 rotates in the direction indicated by the arrow associated therewith. The precursor material 1002 passes through a nip 1006 of a weakening roller (or overbonding) arrangement 1008 formed by rollers 1010 and 1012, thereby forming a weakened or overbonded precursor material. The weakened or overbonded precursor material 1002 has a pattern of overbonds, or densified and weakened areas, after passing through the nip 1006. At least some of, or all of, these overbonds may be used to form apertures in the precursor material 1002. As such, at least some of the overbonds may correlate generally to the patterns of apertures created in the precursor material 1002. The overbonds may be uniform and homogenous or may have a pattern that is non-uniform and/or nonhomogeneous. In other instances, the overbonds may not be ruptured into apertures and the overbonds themselves may form the discrete zones of modified surface energy in a web or topsheet.

Figure 37:
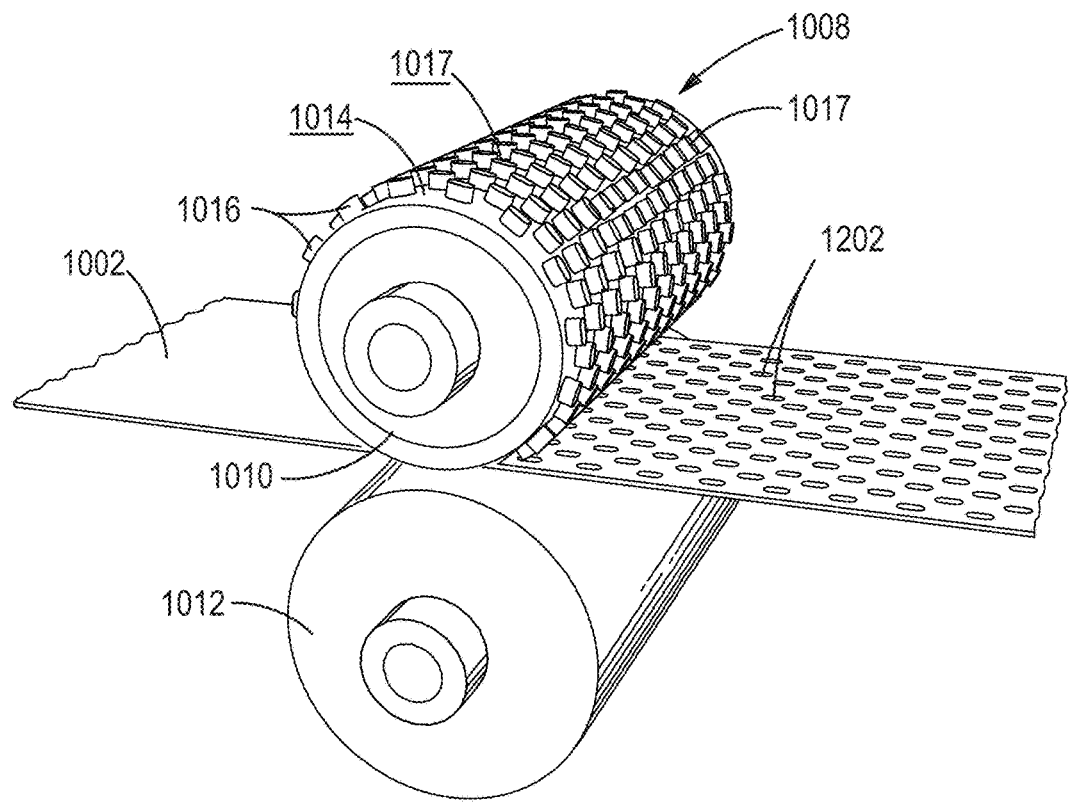
FIG. 37 is a perspective view of an example web weakening arrangement of the process of FIG. 36.

Referring to FIG. 37, the precursor material weakening roller arrangement 1008 may comprises a calendar roller 1010 and a smooth anvil roller 1012. One or both of the patterned calendar roller 1010 and the smooth anvil roller 1012 may be heated and the pressure between the two rollers may be adjusted by known techniques to provide the desired temperature, if any, and pressure to concurrently weaken and melt-stabilize (i.e., overbond) the precursor material 1002 at a plurality of locations 1202. The temperature and/or pressured should be sufficient to render the discrete zones of modified surface energy (i.e., the bonded areas) hydrophilic or hydrophobic as desired. After the precursor material 1002 passes through the weakening roller arrangement 1008, the precursor material 1002 may be stretched in the cross-machine direction ("CD") or generally in the CD, by a cross-machine directional tensioning force to at least partially, or fully, rupture the plurality of weakened, melt stabilized locations 1202, thereby creating a plurality of at least partially formed apertures in the precursor material 1002 coincident with the plurality of weakened, melt stabilized locations 1202. In the context of apertures, the discrete zones of modified surface energy may be formed at least partially around, or fully around, perimeters of the apertures and/or in areas proximate to the apertures (e.g., areas of the overbonds remaining after apertures are formed).

The calendar roller 1010 is configured to have a cylindrical surface 1014, and a plurality of protuberances 1016 which extend radially outwardly from the cylindrical surface 1014. The protuberances 1016 are illustrated as a simplified example of a calendar roller 1010, but more detailed patterned calendar rollers can be used to produce patterned apertured webs, such as that illustrated in FIGS. 32 and 33, for example. The protuberances 1016 may be disposed in a predetermined pattern with each of the protuberances 1016 being configured and disposed to precipitate a weakened, melt-stabilized location in the precursor material 1002 to affect a predetermined pattern of weakened, melt-stabilized locations 1202 in the precursor material 1002. The protuberances 1016 may have a one-to-one correspondence to the pattern of melt stabilized locations in the precursor material 1002.

The protuberances 1016 may have distal end surfaces 1017. The anvil roller 1012 may be a smooth surfaced, circular cylinder of steel, rubber, and/or other material. The anvil roller 1012 and the patterned calendar roller 1010 may be switched in position (i.e., anvil on top) and achieve the same result.

From the weakening roller arrangement 1008, the material 1002 passes through a nip 1030 formed by an incremental stretching system 1032 employing opposed pressure applicators having three-dimensional surfaces which at least to a degree may be complementary to one another.

Figure 38:
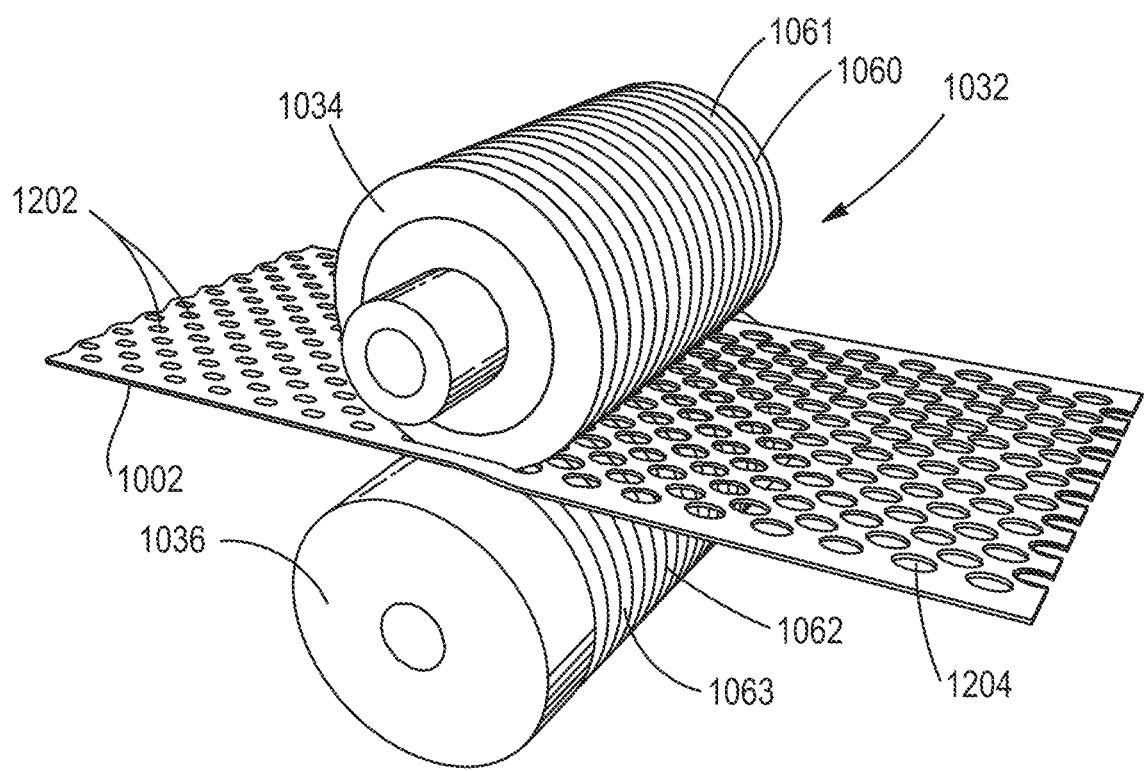
FIG. 38 is a perspective view of an incremental stretching system of the process of FIG. 38.

Referring now to FIG. 38, there is shown a fragmentary enlarged view of the incremental stretching system 1032 comprising two incremental stretching rollers 1034 and 1036. The incremental stretching roller 1034 may comprise a plurality of teeth 1060 and corresponding grooves 1061 which may extend about the entire circumference of roller 1034. The incremental stretching roller 1036 may comprise a plurality of teeth 1062 and a plurality of corresponding grooves 1063. The teeth 1060 on the roller 1034 may intermesh with or engage the grooves 1063 on the roller 1036 while the teeth 1062 on the roller 1036 may intermesh with or engage the grooves 1061 on the roller 1034. The spacing and/or pitch of the teeth 1062 and/or the grooves 1063 may match the pitch and/or spacing of the plurality of weakened, melt stabilized locations 1202 in the precursor material 1002 or may be smaller or larger. As the precursor material 1002 having weakened, melt-stabilized locations 1202 passes through the incremental stretching system 1032, the precursor material 1002 is subjected to tensioning in the CD causing the material 1002 to be extended (or activated) in the CD, or generally in the CD. Additionally, the material 1002 may be tensioned in the MD, or generally in the MD. The CD tensioning force placed on the material 1002 may be adjusted such that it causes the weakened, melt-stabilized locations 1202 to at least partially, or fully, rupture thereby creating a plurality of partially formed, or formed apertures 1204 coincident with the weakened melt-stabilized locations 1202 in the material 1002. However, the bonds of the material 1002 (in the non-overbonded areas) are strong enough such that they do not rupture during tensioning, thereby maintaining the material 1002 in a coherent condition even as the weakened, melt-stabilized locations rupture.

Figure 39:
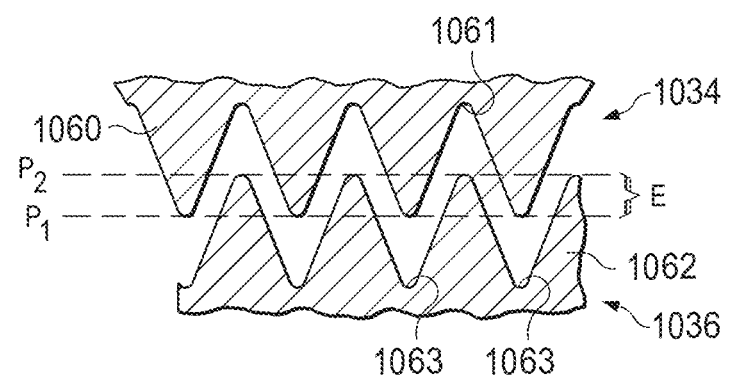
FIG. 39 is an enlarged cross-sectional view showing the details of teeth of the incremental stretching system of FIG. 38.

Referring to FIG. 39, a more detailed view of the teeth 1060 and 1062 and the grooves 1061 and 1063 on the rollers 1034 and 1036 is illustrated. This is known as a "ring rolling" process. The term "pitch" refers to the distance between the apexes of adjacent teeth. The pitch may be between about 0.02 inches to about 0.30 inches or may be between about 0.05 inches and about 0.15 inches, specifically reciting all 0.001 inch increments within the above-specified ranges and all ranges formed therein or thereby. The height (or depth) of the teeth is measured from the base of the tooth to the apex of the tooth, and may or may not be equal for all teeth. The height of the teeth may be between about 0.010 inches and about 0.90 inches or may be between about 0.025 inches and about 0.50 inches, specifically reciting all 0.01 inch increments within the above-specified ranges and all ranges formed therein or thereby. The teeth 1060 in one roll may be offset by about one-half of the pitch from the teeth 1062 in the other roll, such that the teeth of one roll (e.g., teeth 1060) mesh in the valley (e.g., groove 1063) between teeth in the mating roll. The offset permits intermeshing of the two rolls when the rolls are "engaged" or in an intermeshing, operative position relative to one another. The teeth of the respective rolls may only be partially intermeshing in some instances. The degree to which the teeth on the opposing rolls intermesh is referred to herein as the "depth of engagement" or "DOE" of the teeth. The DOE may be constant or not constant. As shown in FIG. 39, the DOE, indicated as "E", is the distance between a position designated by plane P1 where the apexes of the teeth on the respective rolls are in the same plane (0% engagement) to a position designated by plane P2 where the apexes of the teeth of one roll extend inward beyond the plane P1 toward the groove on the opposing roll. The optimum or effective DOE for particular web may be dependent upon the height and the pitch of the teeth and/or the structure of the material. Some example DOEs may be in the range of about 0.01 inches to about 0.5 inches or about 0.03 inches to about 0.2 inches.

As the material 1002 having the weakened, melt-stabilized locations 1202 passes through the incremental web stretching apparatus 1032, the material 1002 is subjected to tensioning in the cross machine direction, or substantially in the cross machine direction (i.e., +/−5 degrees of the cross machine direction) thereby causing the nonwoven web 1002 to be extended in the cross machine direction. The tensioning force placed on the material 1002 may be adjusted by varying the pitch, DOE, or teeth size, such that the incremental stretching is sufficient to cause the weakened, melt-stabilized locations 1202 to at least partially, or fully rupture, thereby creating, or at least partially creating, a plurality of apertures 1204 coincident with the weakened, melt-stabilized locations 1202 in the material 1002. At least some of, or all of, the apertures may comprise a melt lip at least partially surrounding a perimeter of the apertures. The melt lip may be formed by portions of the overbonds.

The material 1002 may comprise bicomponent fibers having a first component and a second component. The first component may comprise a hydrophobic resin or a hydrophobic melt additive. The second component may comprise a hydrophilic resin or a hydrophilic melt additive. The weakened, melt-stabilized locations 1202 and the resulting aperture rims or perimeters of apertures (including the melt lips) may be at least partially hydrophilic owing to the heat and/or energy provided to the material 1002 during overbonding. The heat and/or energy may at least partially move and/or melt the first component and at least partially expose the second component. As such, the second component of the fibers of the material 1002 may be at least partially exposed to render the weakened, melt-stabilized locations 1202 or perimeters of apertures at least partially hydrophilic. The continuous land area may remain hydrophobic as the second component may not be exposed therein. As mentioned above, instead of removing or melting away the first component, the first and second components may be blended in the weakened, melt-stabilized locations 1202 to have a surface energy intermediate a surface energy of the first component and a surface energy of the second component.

Other details regarding the overbonding and ring rolling process to create apertures are disclosed in U.S. Pat. Appl. Publ. No. 2016/0136014, to Arora et al., published on May 19, 2016.

Figure 40:
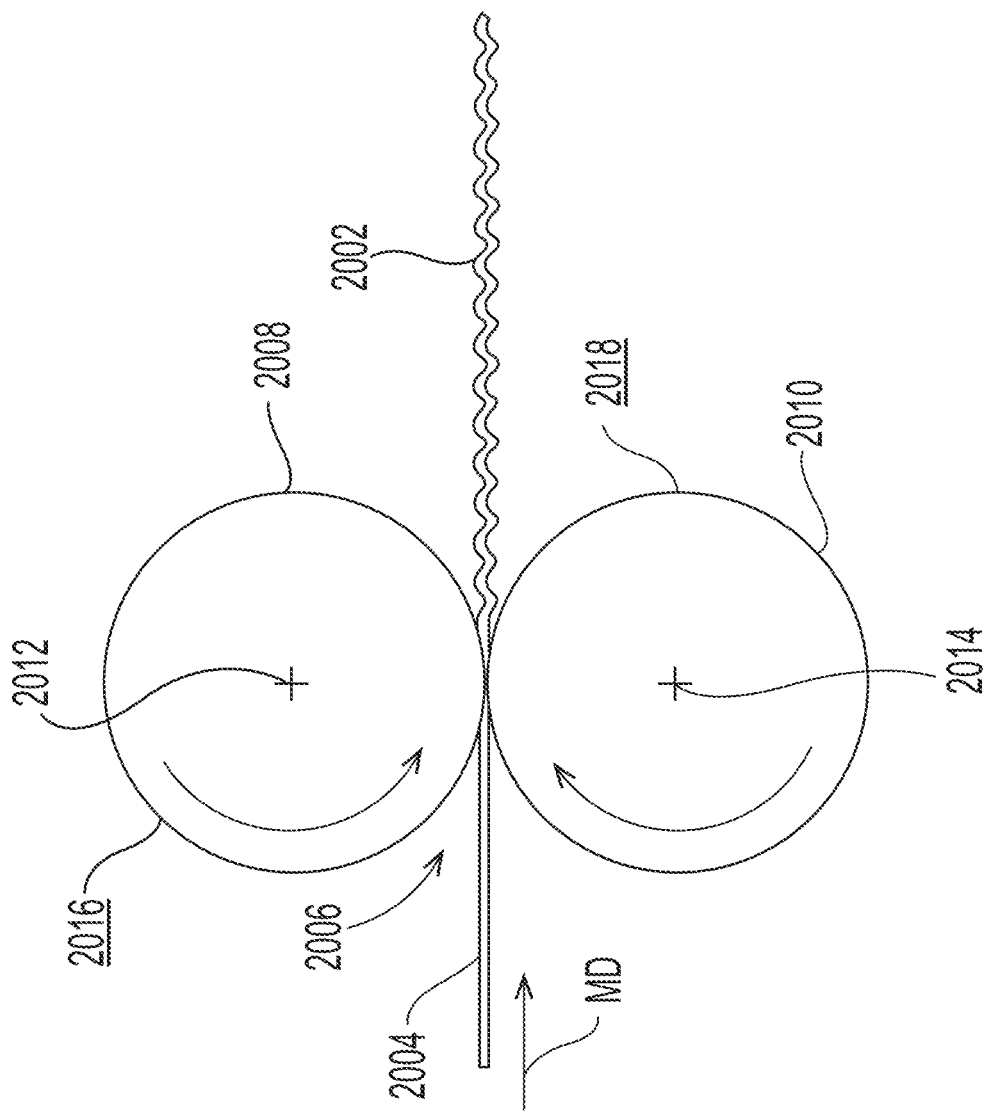
FIG. 40 is a view of a pair of rolls having a web conveyed therebetween.

Referring to FIG. 40, another process of creating apertures and/or three-dimensional elements in a topsheet or web is disclosed. In this process, a precursor material 2004 is conveyed through a nip 2006 between a first roll 2008 and a second roll 2010 to create an apertured and three-dimensional web or topsheet 2002. The precursor material 2004 may be wrapped at least partially around the first roll 2008 or the second roll 2010 to provide better three-dimensional element formation and/or aperture formation. The first roll 2008 may rotate about a first rotational axis 2012 in the direction shown by the arrow and the second roll 2010 may rotate about a second rotational axis 2014 in the direction shown by the arrow. The first roll 2008 may have a first radial outer surface 2016 and the second roll 2010 may have a second radial outer surface 2014.

Figure 41:
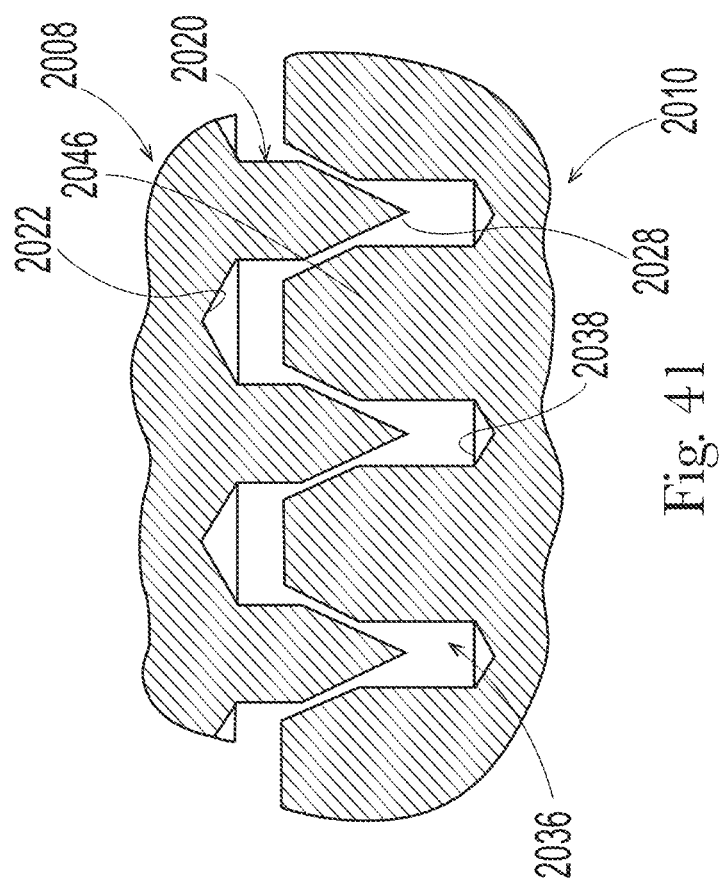
FIG. 41 is a simplified schematic cross-sectional example illustration of a portion of a first roll of FIG. 40 intermeshed with a portion of a second roll of FIG. 40.

FIG. 41 is an example engaged, cross-sectional view of portions of the first and second rolls 2008 and 2010 of FIG. 40 in the nip 2006. The first roll 2008 may comprise a first plurality of projections 2020 each comprising a distal portion 2028 for creating apertures and a first plurality of recesses 2022 defined therein. The second roll 2010 may comprise a second plurality of projections 2036 for creating three-dimensional elements in the precursor material 2004. The second roll 2010 may comprise a second plurality of recesses 2038 defined therein. The first plurality of projections 2020 may at least partially engage the second plurality of recesses 2038 in the nip 2006. The second plurality of projections 2036 may at least partially engage the first plurality of recesses 2022 in the nip 2006. The distal portions 2028 of the first plurality of projections 2020 may engage shoulders 2046 on the second plurality of projections 2036 and compress portions of the precursor material 2004 positioned therebetween to form compressed areas in the precursor material 2004 around apertures.

The precursor material 2004 may comprise fibers that are bicomponent fibers having a first component and a second component. The first component may comprise a hydrophobic resin or hydrophobic melt additive. The second component may comprise a hydrophilic resin or a hydrophilic melt additive. The compressed areas may have at least some of the hydrophilic second component of the bicomponent fibers exposed due to the heat and/or energy created in the precursor material 2004 intermediate the distal portions 2028 and the shoulders 2046. This may render the compressed areas hydrophilic or at least partially hydrophilic. The compressed areas may form the discrete zones of modified surface energy discussed herein, with the three-dimensional elements forming the continuous land area that is hydrophobic.

Figure 42:
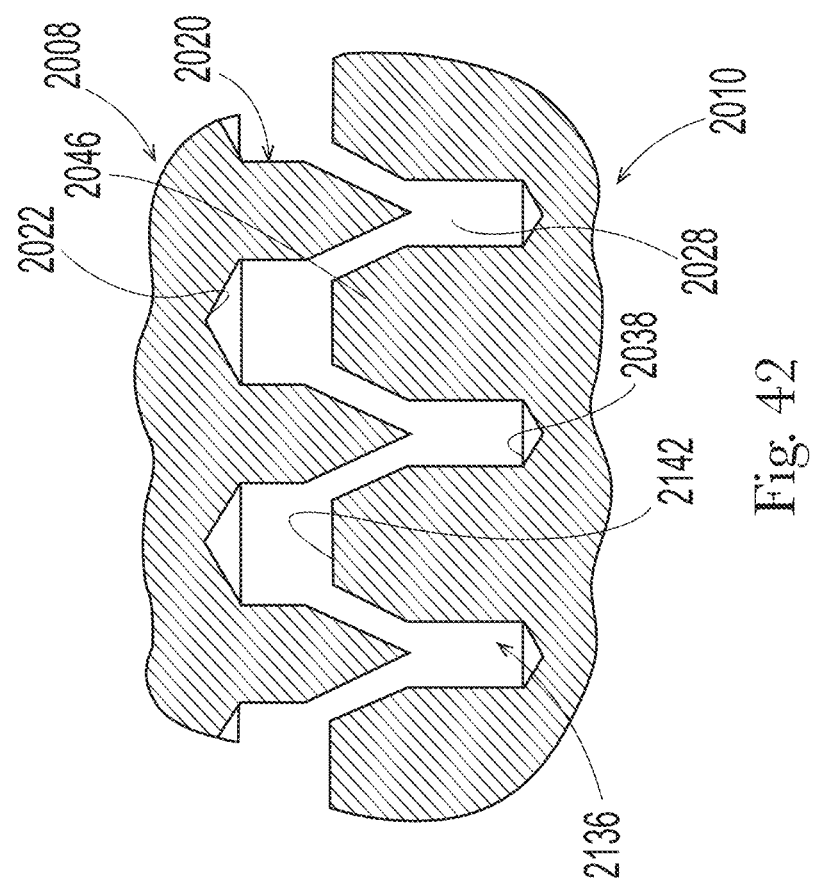
FIG. 42 is another simplified schematic cross-sectional example illustration of a portion of a first roll of FIG. 40 intermeshed with a portion of a second roll of FIG. 40.

FIG. 42 is another example engaged, cross-sectional view of the first and second rolls 2008 and 2010 of FIG. 40 in the nip 2006. The primary difference between FIG. 41 and FIG. 42 is the process only creates apertures in the precursor material and not three-dimensional elements. Compressed areas are still formed intermediate the shoulders 2046 and the distal portions 2028.

Figure 43A:
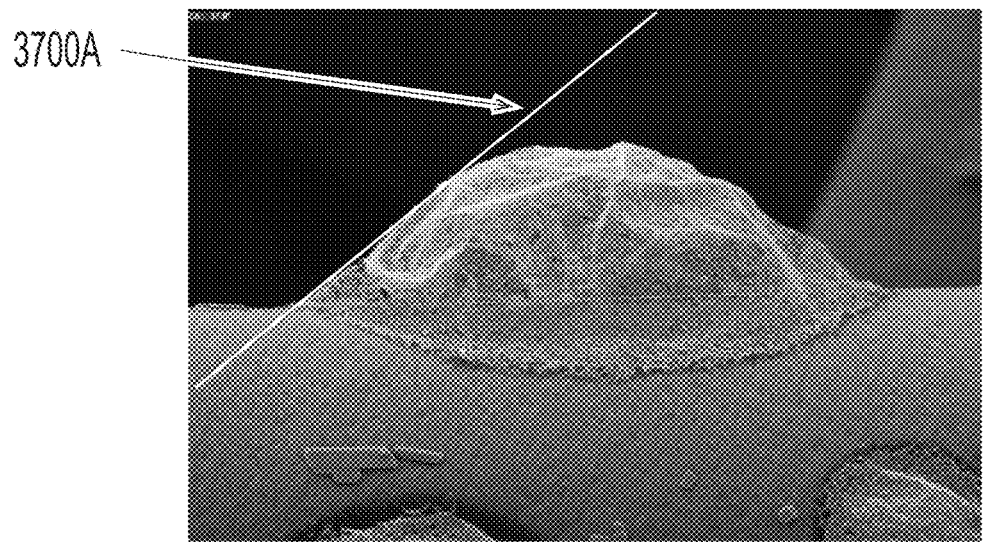
FIGS. 43A-46B are microscope images of water droplets on fibers for the Contact Angle Test herein.
Figure 43B:
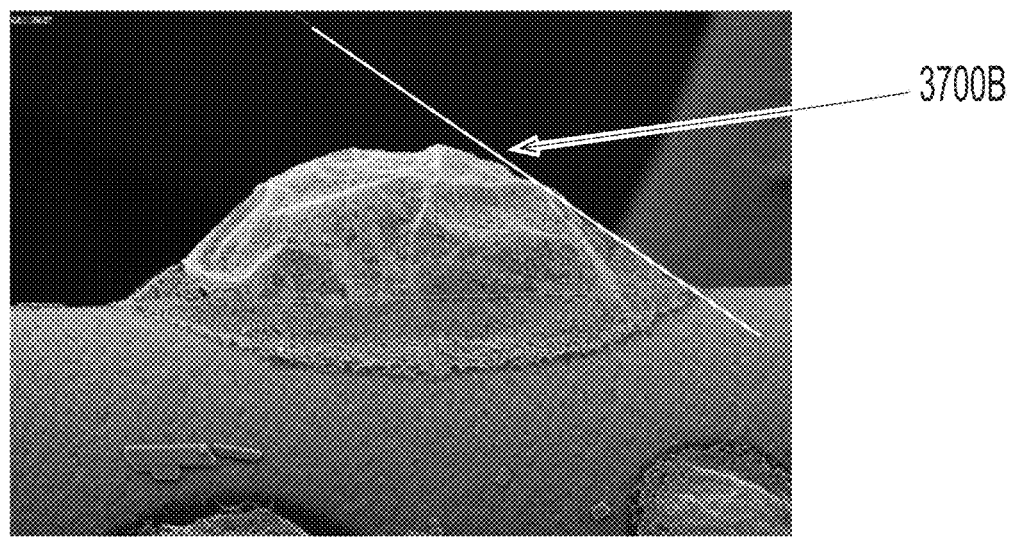
Figure 44A:
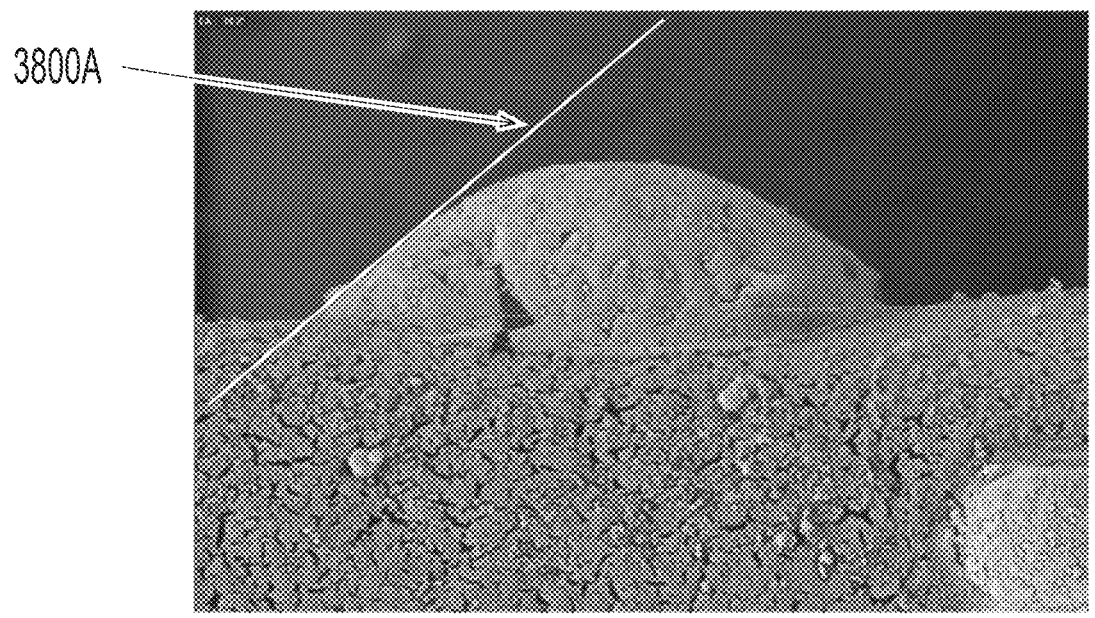
Figure 44B:
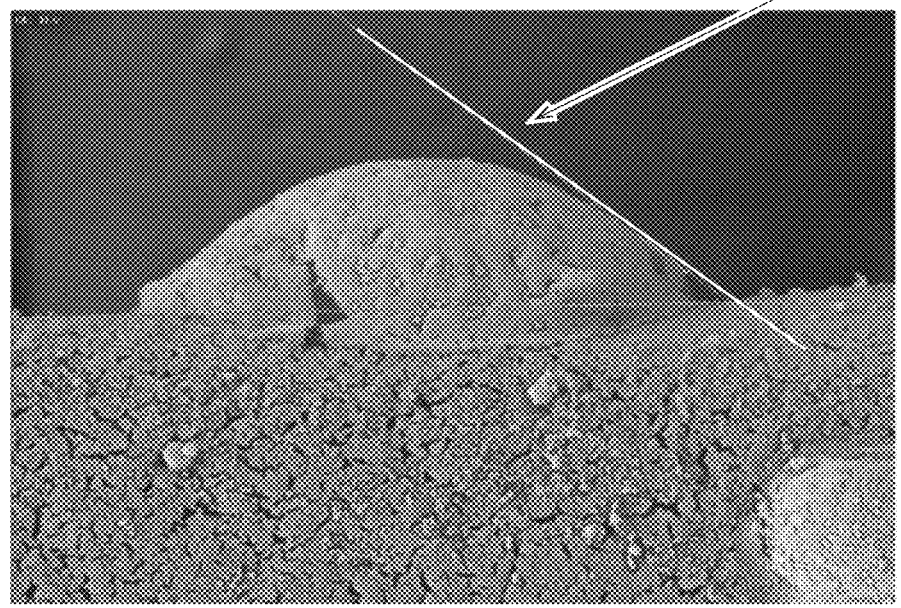
Figure 45A:
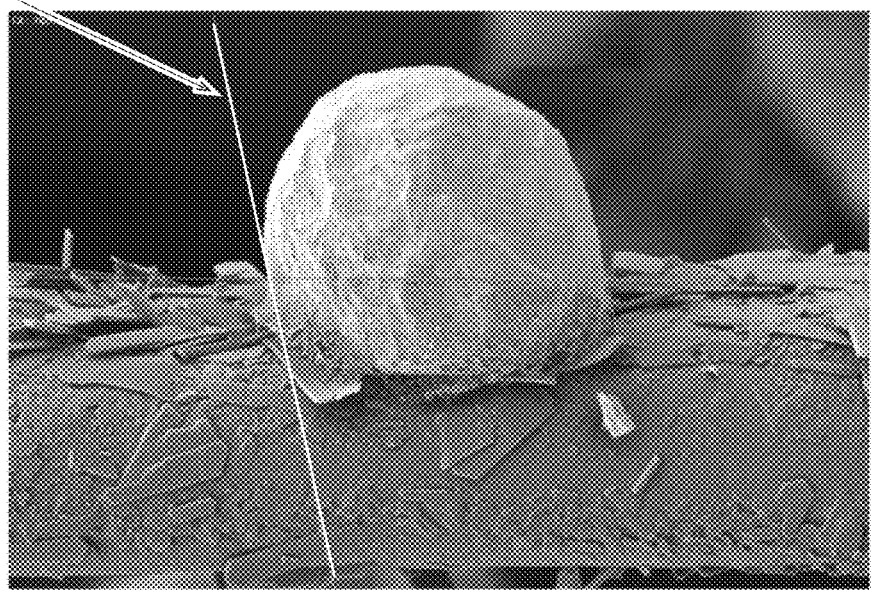
Figure 45B:
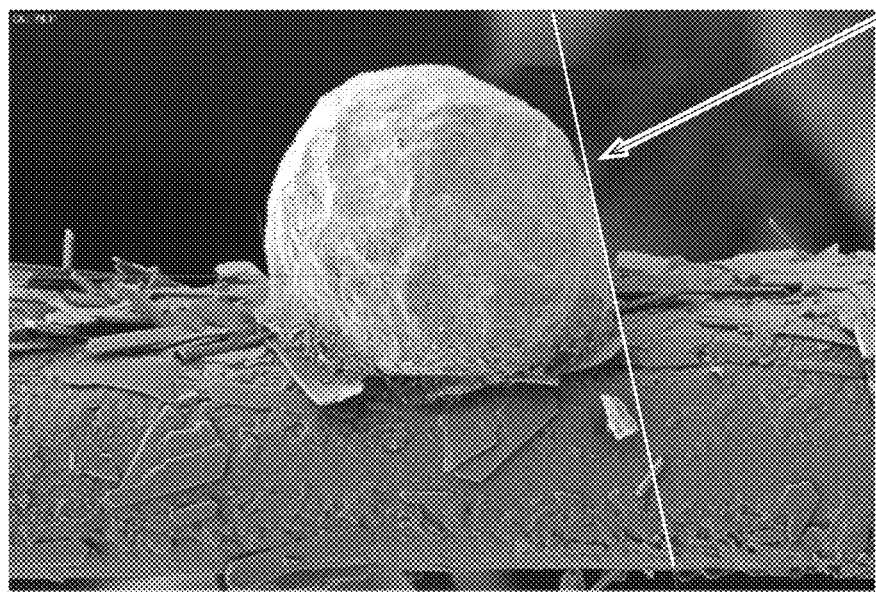
Figure 46A:
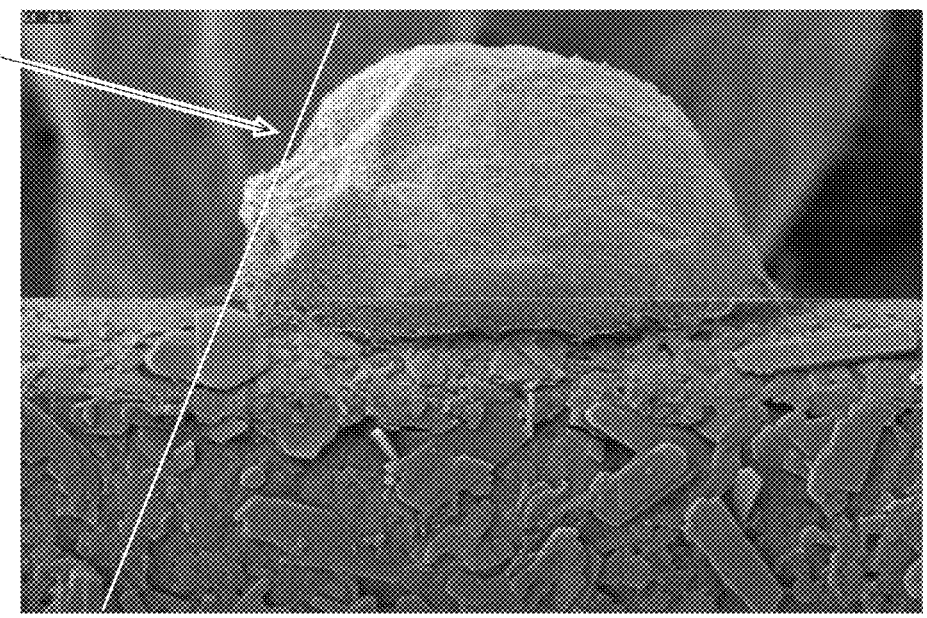
Figure 46B:
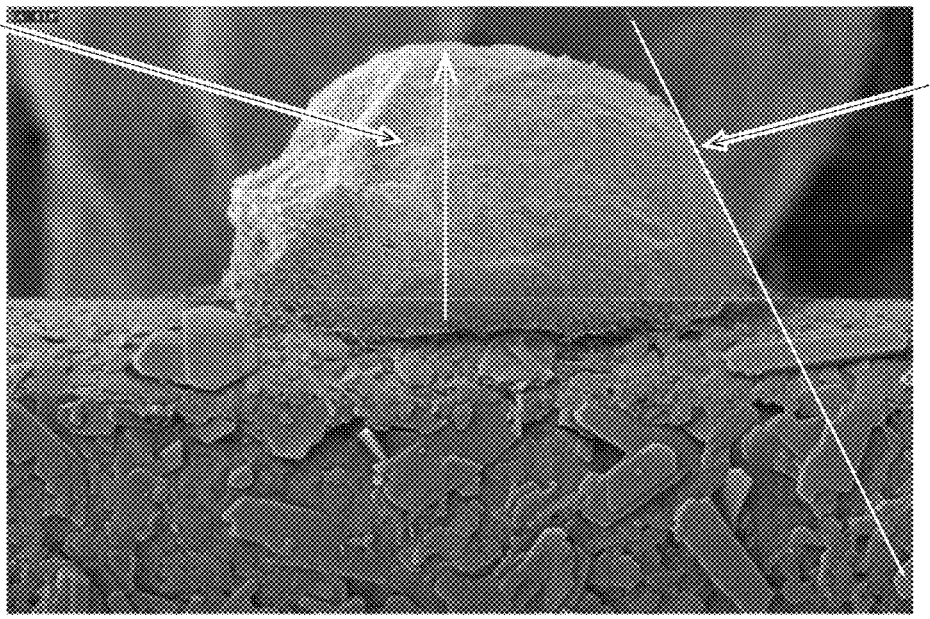

Further details regarding the process illustrated in FIGS. 42-44 are described in U.S. patent application Ser. No. 15/893,727, to Jan Michael Trinkaus et al., filed on Feb. 12, 2018.

The discrete zones of modified surface energy may also be created in a web or topsheet using the process described in U.S. Pat. No. 7,682,686, to Curro et al., issued on Mar. 23, 2010.

The discrete zones of modified surface energy may also be created in a web or topsheet using a standard embossing process, a heated embossing process, and/or a bonding process, such as a calendar or through-air bonding process or other suitable process of inducing heat, pressure, and/or energy. The discrete zones of modified surface energy may also be formed by laser ablation.

Methods of Manufacturing Webs and/or Topsheets

The present disclosure is directed, in part to a method of manufacturing a nonwoven web or topsheet comprising discrete zones of modified surface energy. The method may comprise providing a web comprising bicomponent fibers, wherein at least some of the bicomponent fibers each comprise a first component and a second component. The fibers may also be tricomponent fibers. The first component may comprise a hydrophobic resin or a hydrophobic melt additive. The second component may comprise a hydrophilic resin or a hydrophilic melt additive. Alternatively, the first component may comprise a hydrophilic resin or a hydrophilic melt additive with the second component comprising a hydrophobic resin or hydrophobic melt additive. The method may comprise providing a continuous land area in the web. In the continuous land area, the first component may surround the second component in the fibers and the second component may not be exposed to maintain the continuous land area hydrophobic (or hydrophilic depending on what component is hydrophobic/hydrophilic). The method may comprise applying heat or energy to the web to create bonds or apertures in the web to form the discrete zones of modified surface energy within the continuous land area. The application of heat or energy step may occur after any spontaneous blooming of the hydrophilic melt additive and/or the hydrophobic melt additive. In the discrete zones of modified surface energy, the second component is at least partially exposed to render the discrete zones of modified surface energy at least partially hydrophilic (or hydrophobic depending on what component is hydrophobic/hydrophilic). The method may comprise applying heat or energy to form only discrete bonds or applying heat or energy to form only apertures.

The at least some of the bicomponent fibers may be core/sheath type bicomponent fibers. The first component may form the sheath and the second component may form the core. These core/sheath type bicomponent fibers may be concentric or eccentric.

Alternatively, the at least some of the bicomponent fibers may be islands-in-the-sea type bicomponent fibers. The first component may form the sea. The second component may form the islands.

The method may comprise conveying the web in a machine direction. The applying heat or energy step may comprise forming overbonds in the web. The method may comprise stretching the web substantially in a cross-machine direction to at least partially rupture at least some of the overbonds and at least partially form apertures and forming the discrete zones of modified surface energy at least partially on perimeters of the apertures.

Alternatively, the applying heat or energy step may comprise pin aperturing the web to form apertures. The discrete zones of modified surface energy may be formed on perimeters of the apertures and/or in areas adjacent to the perimeters of the apertures.

The nonwoven topsheet may be formed of a single layer and may be free of topical, surface energy modifying, treatments or printed, surface energy modifying, treatments.

The present disclosure is directed, in part, to a method of manufacturing a single layer, nonwoven topsheet comprising discrete zones of modified surface energy. The method may comprise providing a web comprising bicomponent fibers. At least some of the bicomponent fibers each may comprise a first component and a second component. The first component may comprise a hydrophobic resin or a hydrophobic melt additive. The second component may comprise a hydrophilic resin or a hydrophilic melt additive. The method may comprise conveying the web in a machine direction and providing a continuous land area in the web. In the continuous land area, the first component may surround the second component and the second component may not be exposed to maintain the continuous land area hydrophobic. The method may comprise applying heat or energy to the web to create discrete overbonds in the web within the continuous land area and stretching the web substantially in a cross-machine direction to at least partially rupture at least some of the overbonds in the web and at least partially form apertures. The application of heat or energy step may occur after any spontaneous blooming of the hydrophilic melt additive and/or the hydrophobic melt additive. The discrete zones of modified surface energy may be at least partially formed on perimeters of the apertures and/or in areas proximate to the perimeters of the apertures. The second component may be at least partially exposed in the discrete zones of modified surface energy to render the perimeters of the apertures at least partially hydrophilic. The at least some of the bicomponent fibers may be core/sheath type bicomponent fibers. The first component may form the sheath and the second component may form the core. Alternatively, the at least some of the bicomponent fibers may be islands-in-the-sea type bicomponent fibers. The first component may form the sea and the second component may form the islands.

The discrete zones of modified surface energy herein are not formed by through-air bonding, but may be formed on a through-air bonded base substrate.

The hydrophilic melt additives disclosed as the second component of the bicomponent fibers herein may spontaneously bloom until they reach some equilibrium state. This spontaneous blooming, however, may be contained by the hydrophobic resins or the hydrophobic melt additives disclosed herein. As such, the hydrophilic melt additive spontaneously blooming is not the process by which the discrete zones of modified surface energy are formed. Instead, these discrete zones of modified surface energy are formed after any spontaneous blooming has occurred. Stated another way, any spontaneous blooming of the hydrophilic melt additive is separated in time from creating or exposing of the discrete zones of modified surface energy. The hydrophobic melt additives disclosed as the first component of the bicomponent fibers may also spontaneously bloom until they reach some equilibrium state.

EXAMPLE

Fluid Handling of Apertured Webs or Topsheets

C1 (Comparative Example 1) and Web of the Present Disclosure

Overbonds were created by running a nonwoven web between a heated anvil roll and pattern roll at 900 ft/min at conditions sufficient to generate flow of the polymers in the nonwoven web. (See process and related description of FIG. 37)

C2 (Comparative Example 2)

Overbonds were created by running the nonwoven web between an ultrasonic horn and patterned plate under conditions sufficient to generate flow of the polymers in the nonwoven web.

All Samples

The overbonded webs of C1, C2, and the Present Disclosure were hand cranked through a 0.060" pitch ring roll, set to a depth of engagement ("E" of FIG. 39) of 0.085" to create the apertures. (See FIGS. 38 and 39 and related description, although this example was done by hand, the process is the same.) The aperture patterns of the webs are generally represented in FIG. 31.

Images of the apertured webs (C1, C2, and the Web of the Present Disclosure) were collected by taking images of the webs over a black background using a Nikon D7100 equipped with an AF Micro Nikkor 60 mm, 1:2.8D lens. The following ImageJ macro was used to measure the Aperture Area and % Open Area after setting the scale from an image of a ruler.

run("Make Binary");
  run("Convert to Mask");
  run("Fill Holes");
  run("Analyze Particles . . . ", "size=0.5—Infinity display exclude include summarize add in_situ");
  roiManager("Show All with labels");
  roiManager("Show All");
  run("Flatten")

| Web Sample | Aperture Area (mm2) | | % Open Area | |
| --- | --- | --- | --- | --- |
| | Average | Standard Deviation | Average | Standard Deviation |
| C1 | 2.4 | 1.2 | 18.7 | 1.0 |
| C2 | 2.3 | 1.0 | 21.6 | 1.0 |
| Present Disclosure | 2.4 | 0.5 | 18.1 | 0.2 |

C1=100% hydrophobic web comparative example (25 gsm, PE/PP bicomponent fibers with 17% masterbatch comprising 40% glyceryl tristearate in the PE Sheath)

C2=100% hydrophilic web comparative example (25 gsm, PE/PP bicomponent fibers coated with 0.45 wt % PHP26)

Present Disclosure Example=25 gsm spunbond web having approximately 20 micron diameter sheath/core bicomponent fibers. The sheath was polyethylene (Dow Aspun™ 6850A) and a hydrophobic masterbatch comprising glyceryl tristearate. The core was polypropylene (Exxon Mobile PP3155), TiO2, and a hydrophilic masterbatch (PPM15560 from Techmer).

| Web Sample | 1st Gush Acquisition Speed (seconds) | Rewet (grams) | Stain Intensity (Chroma) |
| --- | --- | --- | --- |
| C1 (hydrophobic) | 120 | 0.1 | 15.6 |
| C2 (hydrophilic) | 4.3 | 0.5 | 27.1 |
| Present Disclosure | 22.0 | 0.4 | 11.0 |

The methods to determine the $1^{st}$ Gush Acquisition Speed, Rewet, and the Stain Intensity (Chroma) can be found in U.S. Provisional Patent Application No. 62/527,288 (14894P), filed on Jun. 30, 2017, to Misael Omar AVILES et al.; U.S. Provisional Patent Application No. 62/527,333 (14895P), filed on Jun. 30, 2017, to Yonas GIZAW et al.; and U.S. Provisional Patent Application No. 62/527,368 (14896P), filed on Jun. 30, 2017, to Misael Omar AVILES et al.

Observations from Example:

The nonwoven webs or topsheets of the present disclosure have a first gush acquisition speed much faster than a single layer hydrophobic web (C1). The nonwoven webs or topsheets of the present disclosure have a lower rewet than a single layer hydrophilic web (C2). The nonwoven webs or topsheets of the present disclosure have the lowest stain intensity (i.e., best masking) than both the hydrophilic web (C1) and the hydrophobic web (C2).

Contact Angle Test

A rectangular specimen measuring 1 cm×2 cm is cut from the topsheet of a disposable absorbent article taking care not to touch the surface of the specimen or to disturb the structure of the material. The specimen coincides with a region of interest of the topsheet of the absorbent article, with the length of the specimen (2 cm) aligned with a central longitudinal axis of the absorbent article. The specimen is handled gently by the edges using forceps and is mounted flat with the skin-facing side up on an SEM specimen holder using double-sided tape. The specimen is sprayed with a fine mist of water droplets generated using a small hobby airbrush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. This is further discussed with regard to FIGS. 43A-46B. The contact angle between the droplet and the fiber is determined directly from the images taken as is shown via lines 3700A, 3700B, 3800A, 3800B, 3900A, 3900B, 4000A, and 4000B. Twenty separate droplets are imaged from which forty contact angle measurements are performed (one on each side of each imaged droplet), and the arithmetic average of these forty contact angle measurements is calculated and reported as the contact angle for that specimen.

Examples of images are provided with regard to FIGS. 25-30. FIGS. 25 and 26 are example images depicting water droplets cryogenically frozen on fibers in a portion of a continuous land area. FIGS. 27 and 28 are example images depicting water droplets cryogenically frozen on calendar bond in the same sample. FIGS. 29 and 30 are example images depicting water droplets cryogenically frozen on the overbond. As noted previously, the projection of the droplet should be maximized to ensure that the appropriate contact angle is measured.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. An absorbent article comprising:
a nonwoven topsheet;
a backsheet; and
an absorbent core positioned at least partially intermediate the topsheet and the backsheet;
wherein the nonwoven topsheet comprises:
a plurality of bicomponent fibers each comprising a hydrophilic core and a hydrophobic sheath,
wherein each hydrophilic core comprises a hydrophilic melt additive,
wherein each hydrophobic sheath comprises a hydrophobic melt additive,
a continuous land area comprising a first portion of the plurality of bicomponent fibers, the first portion having an unmodified core/sheath configuration in which the hydrophilic core is surrounded by the hydrophobic sheath,
wherein the continuous land area is hydrophobic; and
discrete zones of modified surface energy comprising a second portion of the plurality of bicomponent fibers, the second portion having a modified core/sheath configuration in which at least a portion of the hydrophilic core is not surrounded by the hydrophobic sheath,
wherein the discrete zones of modified surface energy are hydrophilic,
wherein at least a majority of the discrete zones of modified surface energy are surrounded by the continuous land area.

2. The absorbent article of claim 1, wherein the discrete zones of modified surface energy comprise bonds.

3. The absorbent article of claim 2, wherein the bonds comprise calendar bonds or point bonds.

4. The absorbent article of claim 1, wherein the discrete zones of modified surface energy comprise perimeter portions at least partially surrounding apertures in the topsheet.

5. The absorbent article of claim 4, wherein the perimeter portions of the apertures are at least partially formed by ruptured bonds.

6. The absorbent article of claim 1, wherein the nonwoven topsheet is formed of only a single layer.

7. The absorbent article of claim 1, wherein the discrete zones of modified surface energy comprise increased permeability zones.

8. The absorbent article of claim 1, wherein the at least some of the bicomponent fibers comprise spunbond fibers or staple fibers.

9. The absorbent article of claim 1, wherein the topsheet is free of topical surface energy modifying treatments.

10. An absorbent article comprising:
a nonwoven topsheet;
a backsheet; and
an absorbent core positioned at least partially intermediate the topsheet and the backsheet;
wherein the nonwoven topsheet comprises:
a plurality of bicomponent fibers, wherein the bicomponent fibers comprise a hydrophobic melt additive and a hydrophilic melt additive;
a continuous land area comprising the bicomponent fibers; and
discrete zones of modified surface energy comprising the bicomponent fibers, wherein at least a majority of the discrete zones of modified surface energy are surrounded by the continuous land area;
wherein, in the continuous land area, the hydrophilic melt additive is not exposed to maintain the continuous land area hydrophobic;
wherein, in at least some of the discrete zones of modified surface energy, the—hydrophilic melt additive is at least partially exposed to render the discrete zones of modified surface energy hydrophilic; and
wherein the nonwoven topsheet is formed of only a single layer; wherein the nonwoven topsheet is not a laminate.

11. The absorbent article of claim 10, wherein the discrete zones of modified surface energy comprise bonds.

12. The absorbent article of claim 11, wherein the bonds comprise calendar bonds or point bonds.

13. The absorbent article of claim 10, wherein the discrete zones of modified surface energy comprise perimeter portions at least partially surrounding apertures in the topsheet.

14. The absorbent article of claim 13, wherein the perimeter portions of the apertures are at least partially formed by ruptured bonds.

15. The absorbent article of claim 10, wherein the discrete zones of modified surface energy comprise increased permeability zones.

16. The absorbent article of claim 10, wherein the at least some of the bicomponent fibers comprise spunbond fibers or staple fibers.

17. The absorbent article of claim 10, wherein the topsheet is free of topical surface energy modifying treatments.

* * * * *